(12) United States Patent
Ichihara et al.

(10) Patent No.: US 7,099,432 B2
(45) Date of Patent: Aug. 29, 2006

(54) X-RAY INSPECTION APPARATUS AND X-RAY INSPECTION METHOD

(75) Inventors: Masaru Ichihara, Ashiya (JP); Shinji Yoshino, Nishinomiya (JP); Hiroyuki Inoue, Yawata (JP); Toshio Kinoshita, Katano (JP); Kazuo Ohuchi, Hojo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/924,363

(22) Filed: Aug. 23, 2004

(65) Prior Publication Data

US 2005/0074088 A1     Apr. 7, 2005

(30) Foreign Application Priority Data

Aug. 27, 2003 (JP) .............................. 2003-303188
Sep. 22, 2003 (JP) .............................. 2003-330180

(51) Int. Cl.
  *G01N 23/083* (2006.01)
(52) U.S. Cl. ............................. 378/25; 378/21; 378/208
(58) Field of Classification Search ................ 378/208, 378/24, 57, 21, 23, 118, 117, 199, 127, 25–27
  See application file for complete search history.

(56) References Cited

U.S. PATENT DOCUMENTS

| | | | |
|---|---|---|---|
| 4,926,452 A | | 5/1990 | Baker et al. |
| 5,848,115 A | * | 12/1998 | Little et al. ..................... 378/4 |
| 6,628,746 B1 | * | 9/2003 | Eppler et al. .................. 378/21 |
| 6,687,328 B1 | * | 2/2004 | Bavendiek et al. ........... 378/58 |

FOREIGN PATENT DOCUMENTS

| | | |
|---|---|---|
| JP | 59-116040 | 7/1984 |
| JP | 11-344453 | 12/1999 |
| JP | 2002-189002 A | 7/2002 |

\* cited by examiner

*Primary Examiner*—Edward J. Glick
*Assistant Examiner*—Hoon Song
(74) *Attorney, Agent, or Firm*—Pearne & Gordon LLP

(57) ABSTRACT

The X-ray inspection device and the X-ray inspection method according to the present invention are configured to hold an object to be inspected irradiated with an X-ray from an X-ray irradiation device, uses a swinging device for performing swinging motion of tilting the object to be inspected at an arbitrary angle and in an arbitrary direction, images the X-ray that passes through the object to be inspected in an X-ray detection device and extracts data of a desired cross section from the X-ray image of the X-ray detection device in a control device.

13 Claims, 21 Drawing Sheets

-- PRIOR ART --

-- PRIOR ART --

-- PRIOR ART --

X-RAY INSPECTION APPARATUS AND X-RAY INSPECTION METHOD

BACKGROUND OF THE INVENTION

The present invention relates to an X-ray inspection device, for example, an X-ray inspection device and an X-ray inspection method that inspect the bonding condition of a component mounted on a printed circuit board, the bonding condition of the inside of a component packaged with resin or metal and the bonding condition of a component packaged within a printed circuit board.

In these years, devices such as PDA [personal digital assistant] have been miniaturized and upgraded, and in packaging electronic components in the devices, to package as many electronic components as possible in small space, increase in packaging density, face-down bonding of bonding an electrode provided on a lower face of the electronic components to a land of a printed circuit board, and built-in of electronic components of packaging the electronic components within a printed circuit board have been promoted.

Since a bonded part by the above-mentioned face-down bonding or a bonded part in the case of the packaging within a printed circuit board cannot be viewed directly, an inspection method of exposing a cross section of the bonded part and viewing the exposed cross section and a nondestructive X-ray inspection method of viewing the internal condition of an object to be inspected are used. When using the X-ray inspection method, it is possible to view the bonding condition of the inside of the object to be inspected. However, in the case that a plurality of components are packaged with being overlapped with each other, the components overlap each other in an X-ray image and therefore it is difficult to view the condition of each component accurately. For this reason, in conventional X-ray inspection devices, the object to be inspected is imaged at a plurality of positions by varying a direction of X-ray irradiation and an irradiation angle with respect to the object to be inspected, and a cross-sectional part to be viewed is taken from the X-ray image according to tomography or laminography and then viewed and inspected.

The conventional X-ray inspection device will be described below with reference to the appended drawings. The elements common to each conventional example are described by assigning the same reference numerals.

FIG. 18 is a block diagram showing the schematic configuration of a conventional X-ray inspection device by using tomography. The conventional X-ray inspection device shown in FIG. 18 is disclosed in, for example, the Official Gazette of Japanese Unexamined Patent Publication No. Hei 11-344453.

As shown in FIG. 18, an X-ray is irradiated from an X-ray irradiation device 103 into an object to be inspected 102 such as a printed circuit board held by a rotation device 101 and the X-ray that passes through the object to be inspected 102 is detected by an X-ray detection device 100. The X-ray irradiation device 103 is located on a direct extension of the rotation center of the rotation device 101 and an imaging center of the X-ray detection device 100 and emits the X-ray toward the X-ray detection device 100. A control device 104 controls the rotation position of the rotation device 101 and controls driving of the X-ray detection device 100 and the X-ray irradiation device 103. The control device 104 controls so that the X-ray irradiation device 103 radiates an X-ray when the rotation device 101 that holds the object to be inspected 102 is rotated at a predetermined rotation angle and the X-ray image passed through the object to be inspected 102 is captured in the X-ray detection device 100. At this time, the control device 104 is configured so as to allow the rotation device 101 to rotate one or a half revolution and the X-ray detection device 100 to take an image, and prepare an X-ray image of the cross-sectional part image to be viewed and display it.

As mentioned above, the conventional X-ray inspection device shown in FIG. 18 is configured so as to rotate the object to be inspected 102 around an axis orthogonal to an X-ray irradiation axis as a rotation axis. In the configuration of the conventional X-ray inspection device shown in FIG. 18, a distance A between an X-ray focus (spot position) of an X-ray source that the X-ray irradiation device 103 emits the X-ray and the rotation axis of the object to be inspected 102 and a distance B between the position of this rotation axis and a detection part of the X-ray detection device 100 are constrained by an outside dimension of the object to be inspected 102. This constraint means that a minimum value of the distance A must meet a condition of A>C/2 so that the outside dimension (dimension indicated by C in FIG. 18) of a printed circuit board as the object to be inspected 102 can rotate. Due to the constraint, the object to be inspected 102 cannot get closer to the X-ray irradiation device 103 so much. In the conventional X-ray inspection device shown in FIG. 18, in the case when the distance A+B that defines an arrangement space of object to be inspected is reduced, a value of A in (A+B)/A as a magnifying factor of the X-ray image is limited and therefore the magnifying factor cannot be increased. For this reason, the conventional X-ray inspection device shown in FIG. 18 has a problem that it is difficult to view a detailed condition of each component.

FIG. 19 is a block diagram showing a schematic configuration of a conventional X-ray inspection device by using laminography. The conventional X-ray inspection device shown in FIG. 19 is disclosed in, for example, the specification of U.S. Pat. No. 4,926,452.

In FIG. 19, a rotational X-ray irradiation device 105 has a function of controlling a thermal electron by rotating magnetic field and rotating and irradiating the X-ray at a predetermined position. An X-ray detection device 109 converts the X-ray that passes through the object to be inspected 102 such as a printed circuit board into a visible light in a scintillator 107 and then detects the light through a rotational mirror mechanism 108. A control part 106 controls driving of the rotational mirror mechanism 108 in synchronization with the rotating magnetic field of the rotational X-ray irradiation device 105. Further, the control part 106 controls the rotational X-ray irradiation device 105 and the X-ray detection device 109 for imaging and the X-ray inspection device obtains the tomographic image of the object to be inspected 102 at high speed and carries out inspection.

In the conventional X-ray inspection device shown in FIG. 19, an irradiation angle β with respect to the object to be inspected 102 is a fixed value physically determined in advance. Accordingly, when the object to be inspected 102 is moved closer to the rotational X-ray irradiation device 105, the object to be inspected 102 falls outside of the X-ray irradiation range, for example, at a position indicated by W in FIG. 19. For this reason, there causes a problem that even when the user ties to magnify the X-ray image by moving the object to be inspected 102 closer to the rotational X-ray irradiation device 105, the magnifying factor is constrained. Further, the conventional X-ray inspection device shown in FIG. 19 is complicated in configuration and expensive.

In another conventional X-ray inspection device, by slanting and rotating the X-ray irradiation device, and separating bonded parts overlapped with each other within the object to be inspected, the bonding condition of each bonded part is inspected. Such conventional X-ray inspection device is disclosed in, for example, the Official Gazette of Unexamined Patent Publication No. 2002-189002.

FIG. 20 is a view showing the schematic configuration of the conventional X-ray inspection device for inspecting the bonding condition by slanting and rotating the X-ray irradiation device.

The X-ray inspection device shown in FIG. 20 is configured so that an X-ray irradiation device 110 irradiates a printed circuit board and so on as the object to be inspected 102 with an X-ray obliquely. The X-ray radiated from the X-ray irradiation device 110 is configured so as to pass through the object to be inspected 102 and to be received in an X-ray detection device 115. The oblique radiography conducted in the conventional X-ray inspection device is performed by slanting the X-ray irradiation device 110. In this manner, the X-ray detection device 115 takes X-ray radioscopic images of the object to be inspected 102 by irradiating the object to be inspected 102 with the X-ray from various angles. As a result, based on these X-ray radioscopic images, it becomes possible to inspect the condition of the component at a desired position in the object to be inspected 102.

FIG. 21 is a block diagram showing a main part of the conventional X-ray inspection device shown in FIG. 20. In FIG. 21, the object to be inspected 102 is a circuit forming body consisting of a ball grid array 111 (hereinafter referred to as BGA) with a face-down bonded part, a printed circuit board 112 and an electronic component 113. The X-ray irradiation device 110 is slanted with respect to the object to be inspected 102 and the object to be inspected 102 is imaged in the X-ray detection device 115. FIG. 21 shows a scintillator 114 of the X-ray detection device 115.

A radiographic image indicated by F in FIG. 21 is an example of X-ray images at the time when the X-ray irradiation device 110 is located just below the object to be inspected 102 and the X-ray radiated from the X-ray irradiation device 110 shows the state in which components are overlapped with each other in the circuit forming body as the object to be inspected 102. A radiographic image indicated by G in FIG. 21 is an example of X-ray images detected by the X-ray detection device 115 when the X-ray irradiation device 110 is disposed obliquely and irradiates the object to be inspected 102 with the X-ray. Since the electronic component and the bonded part and the like exist in the circuit forming body as the object to be inspected 102 at different positions, the radiographic image F and the radiographic image G are different from each other due to difference in radiographic angle.

As shown in FIG. 21, although all of the bonded parts of BGA 111 cannot be inspected according to only the radiographic image F since the BGA 111 is blocked by the electronic component, the bonding condition of all bonded parts of the BGA 111 can be inspected by using the radiographic image G taken with the X-ray irradiation device 110 being slanted. That is, the position of the electronic component 113 is excluded from the inspected range and the bonded part of BGA is inspected, so that the condition of all bonded parts of the BGA can be inspected in a plurality of the radiographic images.

However, when packaging interval between the electronic components becomes narrower, influence of the electronic components on the different level from the cross section of the object to be inspected cannot be removed at any angle, thereby causing the problem that accurate information on the cross section of the object to be inspected cannot be obtained.

BRIEF SUMMARY OF THE INVENTION

The present invention intends to solve the problems of the conventional various X-ray inspection devices and to provide an X-ray inspection device and an X-ray inspection method capable of acquiring information on a desired cross section accurately even when an interval between components of an object to be inspected becomes narrower, resulting in high density packaging. Moreover, the present invention intends to provide an X-ray inspection device and an X-ray inspection method that can obtain a clear tomographic image with high resolution at lower cost without being restricted by resolution due to the shape of an object to be inspected and perform non-destructive inspection with high precision by using the tomographic image.

To achieve the above-mentioned object, the X-ray inspection device of the present invention has an X-ray irradiation device for generating an X-ray and irradiating an object to be inspected with the X-ray;

an X-ray detection device for detecting the X-ray radiated from the above-mentioned X-ray irradiation device that passes through the above-mentioned object to be inspected;

a swinging device for holding the above-mentioned object to be inspected on an X-ray path from the above-mentioned X-ray irradiation device to the above-mentioned X-ray detection device and driving the above-mentioned object to be inspected at an arbitrary angle in an arbitrary direction with respect to an X-ray irradiation axis on the above-mentioned X-ray path; and a control device for controlling driving of the above-mentioned swinging device and the above-mentioned X-ray irradiation device, receiving an input of an X-ray image data from the above-mentioned X-ray detection device and displaying the above-mentioned X-ray image data.

In the present invention thus constituted, even when a clearance between components of an object to be inspected becomes narrower, resulting in high density packaging, information on a desired cross section can be acquired accurately. Further, in the present invention, with compact and inexpensive configuration, it becomes possible to obtain an X-ray image with high precision in an arbitrary direction and at an arbitrary tilt angle.

An X-ray inspection device from another aspect of the present invention has an X-ray irradiation device for generating an X-ray and irradiating an object to be inspected with the X-ray;

an X-ray detection device for detecting the X-ray radiated from the above-mentioned X-ray irradiation device that passes through the above-mentioned object to be inspected;

a swinging device for holding the above-mentioned object to be inspected on an X-ray path from the above-mentioned X-ray irradiation device to the above-mentioned X-ray detection device and driving the above-mentioned object to be inspected at an arbitrary angle in an arbitrary direction with respect to an X-ray irradiation axis on the above-mentioned X-ray path;

a swinging device for X-ray detection for driving the above-mentioned X-ray detection device in the same direction and at the same angle as the above-mentioned object to be inspected driven by the above-mentioned swinging device; and a control device for controlling driving of the above-mentioned swinging device and the above-mentioned X-ray irradiation device, receiving an input of an X-ray image data from the above-mentioned X-ray detection device and displaying the above-mentioned X-ray image data.

In the present invention thus constituted, with compact and inexpensive configuration, it becomes possible to obtain an X-ray image with high precision in an arbitrary direction and at an arbitrary tilt angle, and by acquiring a tomographic image from a plurality of tilt images by calculation in the control device, the tomographic image with less blur and false echo can be obtained. Further, since tomographic data of a printed circuit board with high packaging density or a thin board can be obtained reliably, the inspection using a clear tomographic image having high resolution becomes possible.

An X-ray inspection device from another aspect of the present invention has an X-ray irradiation device for irradiating an X-ray in the vertical direction in a form of cone with an X-ray focus as a vertex at a predetermined irradiation angle;

a holding mechanism for horizontally holding an object to be inspected within an X-ray irradiation range;

a transfer mechanism for object to be inspected for transferring the above-mentioned object to be inspected held by the above-mentioned holding mechanism to an arbitrary position in the horizontal direction within an X-ray irradiation range;

an X-ray detection device having a detection plane for detecting the X-ray that passes through the above-mentioned object to be inspected;

a transfer mechanism for X-ray detection for transferring the above-mentioned X-ray detection device to an arbitrary position on a plain parallel to the plane to which the above-mentioned object to be inspected is transferred;

a motor control device for controlling driving of the above-mentioned transfer mechanism for object to be inspected and the above-mentioned transfer mechanism for X-ray detection in synchronization with each other;

an image processing device for extracting an X-ray image of an arbitrary cross section from the X-ray image formed by the above-mentioned X-ray detection device; and a display device for displaying the above-mentioned X-ray image formed by the above-mentioned X-ray detection device and the above-mentioned image processing device.

In the present invention thus constituted, the inspected place can be viewed without shifting from the center of the monitor screen while changing radiographic direction and radiographic magnifying factor. Further, from the X-ray image of the cross section of the inspected place, various bonding defects including open defect of the bonded part of the printed circuit board as the object to be inspected can be inspected.

An X-ray inspection method of the present invention has:

attaching an object to be inspected to a swinging device disposed on an X-ray path from an X-ray irradiation device to an X-ray detection device;

driving the above-mentioned object to be inspected by the above-mentioned swinging device at an arbitrary angle in an arbitrary direction with respect to an X-ray irradiation axis on the above-mentioned X-ray path;

irradiating the above-mentioned object to be inspected with the X-ray radiated from the above-mentioned X-ray irradiation device;

detecting the X-ray that passes through the above-mentioned object to be inspected by the above-mentioned X-ray detection device; and receiving an input of an X-ray image data from the above-mentioned X-ray detection device and extracting data on an arbitrary cross section from the above-mentioned X-ray image data.

In the X-ray inspection method of the present invention having these steps, even when a clearance between components of an object to be inspected becomes narrower, resulting in high density packaging, information on a desired cross section can be acquired accurately. Further, in the present invention, it becomes possible to obtain an X-ray image with high precision in an arbitrary direction and at an arbitrary tilt angle of the object to be inspected.

An X-ray inspection method from another aspect of the present invention has:

holding an object to be inspected horizontally within an X-ray irradiation range;

transferring the above-mentioned object to be inspected held by the above-mentioned holding mechanism to an arbitrary position in the horizontal direction within an X-ray irradiation range;

transferring the above-mentioned X-ray detection device to an arbitrary position on a plain parallel to the plane to which the above-mentioned object to be inspected is transferred by a transfer mechanism for X-ray detection so that a target point is located at a center of the X-ray image formed by an X-ray detection device in synchronization with the transfer of the above-mentioned object to be inspected;

irradiating an X-ray in the vertical direction in a form of cone with an X-ray focus as a vertex at a predetermined irradiation angle;

detecting the X-ray that passes through the above-mentioned object to be inspected by the above-mentioned the above-mentioned X-ray detection device;

in an image processing device, extracting an X-ray image of an arbitrary cross section from the X-ray image formed by the above-mentioned X-ray detection device; and displaying the above-mentioned X-ray image formed by the above-mentioned X-ray detection device and the above-mentioned image processing device.

In the X-ray inspection method of the present invention having these steps, the inspected place can be viewed without shifting from the center of the monitor screen while changing radiographic direction and radiographic magnifying factor. Further, from the X-ray image of the cross section of the inspected place, various bonding defects including open defect of the bonded part of the printed circuit board as the object to be inspected can be inspected.

While the novel features of the invention are set forth particularly in the appended claims, the invention, both as to configuration and content, will be better understood and appreciated, along with other objects and features thereof, from the following detailed description taken in conjunction with the drawings.

It will be recognized that some or all of the drawings are schematic representations for purposes of illustration and do not necessarily depict the actual relative sizes or locations of the elements shown.

DETAILED DESCRIPTION OF THE INVENTION

A preferred embodiment of an X-ray inspection device and an X-ray inspection method of the present invention will be described below with referring to the appended drawings.

<<First Embodiment>>

Figure 1:
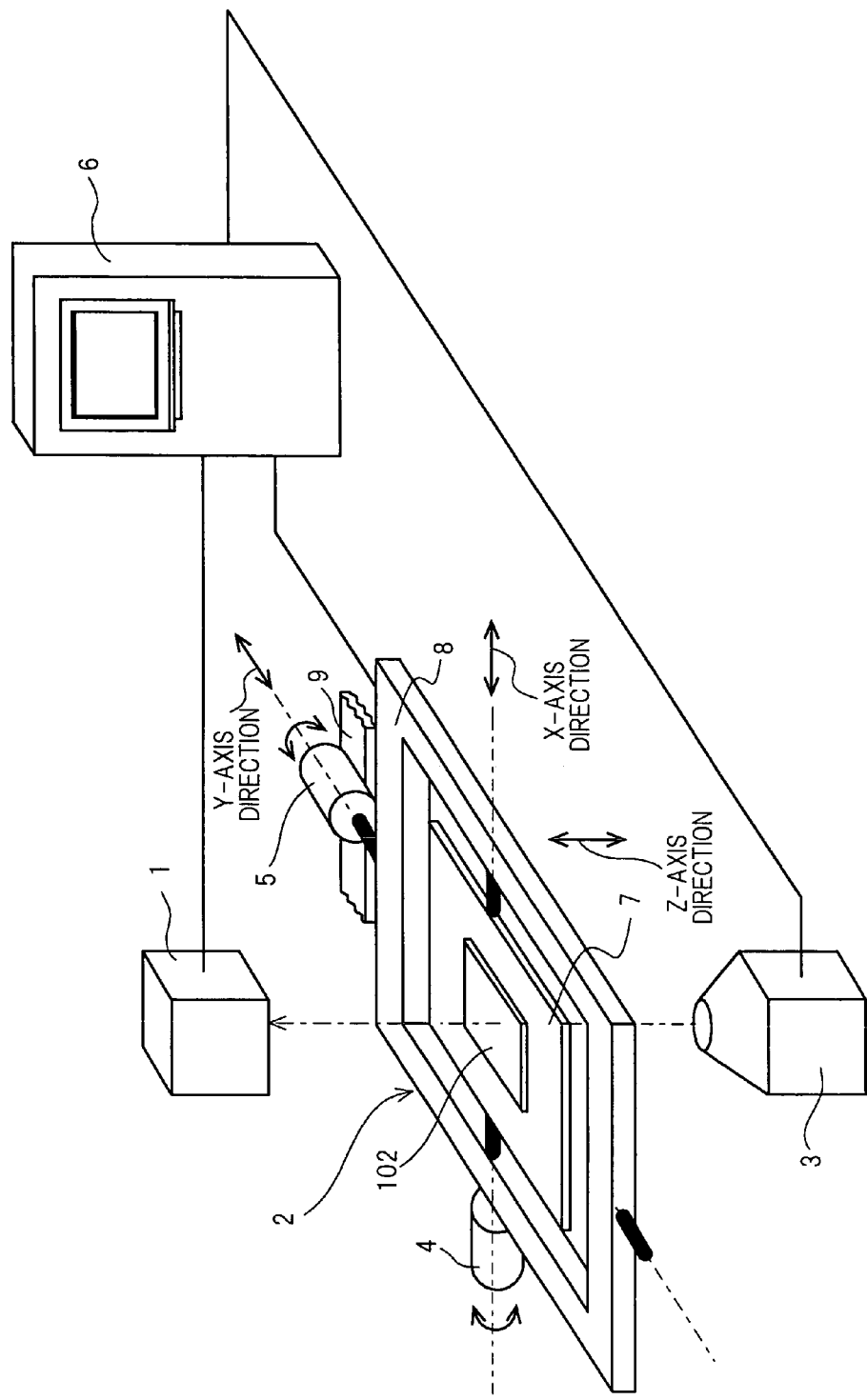
FIG. 1 is a view showing the schematic configuration of an X-ray inspection device in accordance with a first embodiment of the present invention.

FIG. 1 is a view showing a schematic configuration of an X-ray inspection device in accordance with a first embodiment of the present invention.

As shown in FIG. 1, an X-ray radiated from an X-ray irradiation device 3 is irradiated to an object to be inspected 102 held by a swinging device 2, for example, a circuit forming body including a printed circuit board and so on, and the X-ray that passes through the object to be inspected 102 is detected by an X-ray detection device 1. The X-ray irradiation device 3 is located on the extension line connecting the center of the swinging device 2 and the imaging central position of the X-ray detection device 1 (X-ray path) and emits the X-ray toward the X-ray detection device 1. A control device 6 controls transfer of the swinging device 2 in the Z-axis direction (direction of an X-ray irradiation axis) and tilt angles with respect to the X axis and Y axis of the swinging device 2 as well as controls driving of the X-ray detection device 1 and the X-ray irradiation device 3. In the state shown in FIG. 1, a horizontal direction is a Y-axis direction and a direction orthogonal to the Y-axis direction is the X-axis direction. A Z-axis direction is a direction vertical to an X-ray focus (spot position) of the X-ray irradiation device 3, which is the direction of X-ray irradiation axis.

The control device 6 controls driving so that the X-ray is irradiated from the X-ray irradiation device 3 in the state where the swinging device 2 holding the object to be inspected 102 forms a predetermined angle and an X-ray image passing through the object to be inspected 102 is captured in the X-ray detection device 1.

The X-ray inspection device of the first embodiment is configured so that the X-ray that passes through the object to be inspected 102 is captured in the X-ray detection device 1 to form an X-ray image, the X-ray image is calculated in the control device 6 and the calculation result is displayed on the control device 6.

The X-ray irradiation device 3 has the system of utilizing the X-ray generated by hitting accelerated thermal electrons against a target and taking the form of a sealed tube, the internal of which is sealed substantially under vacuum at all times. However, the present invention is not limited to this system and may use an X-ray irradiation device that replaces a filament generating thermal electrons at the user's side and takes the form of an open tube, the internal of which is evacuated at each use. To enhance resolution by increasing the magnifying ratio, it is preferable to minimize an X-ray focus size (spot diameter) of the X-ray source as much as possible. For this reason, in the first embodiment, the X-ray irradiation device 3 having the X-ray focus size of 1 μm is used and a blur of the X-ray image during display is minimized as far as possible.

In the first embodiment, the circuit forming body as the object to be inspected 102 is a printed circuit board, any electronic component, a composite of these elements or a packaging component to which these elements are bonded. The print circuit board covers various boards such as a paper phenol single-sided board, a multi-layer glass epoxy board, a film-like board, a board with built-in electronic components and a board with a resin surface on which a circuit pattern is formed.

Figure 2:
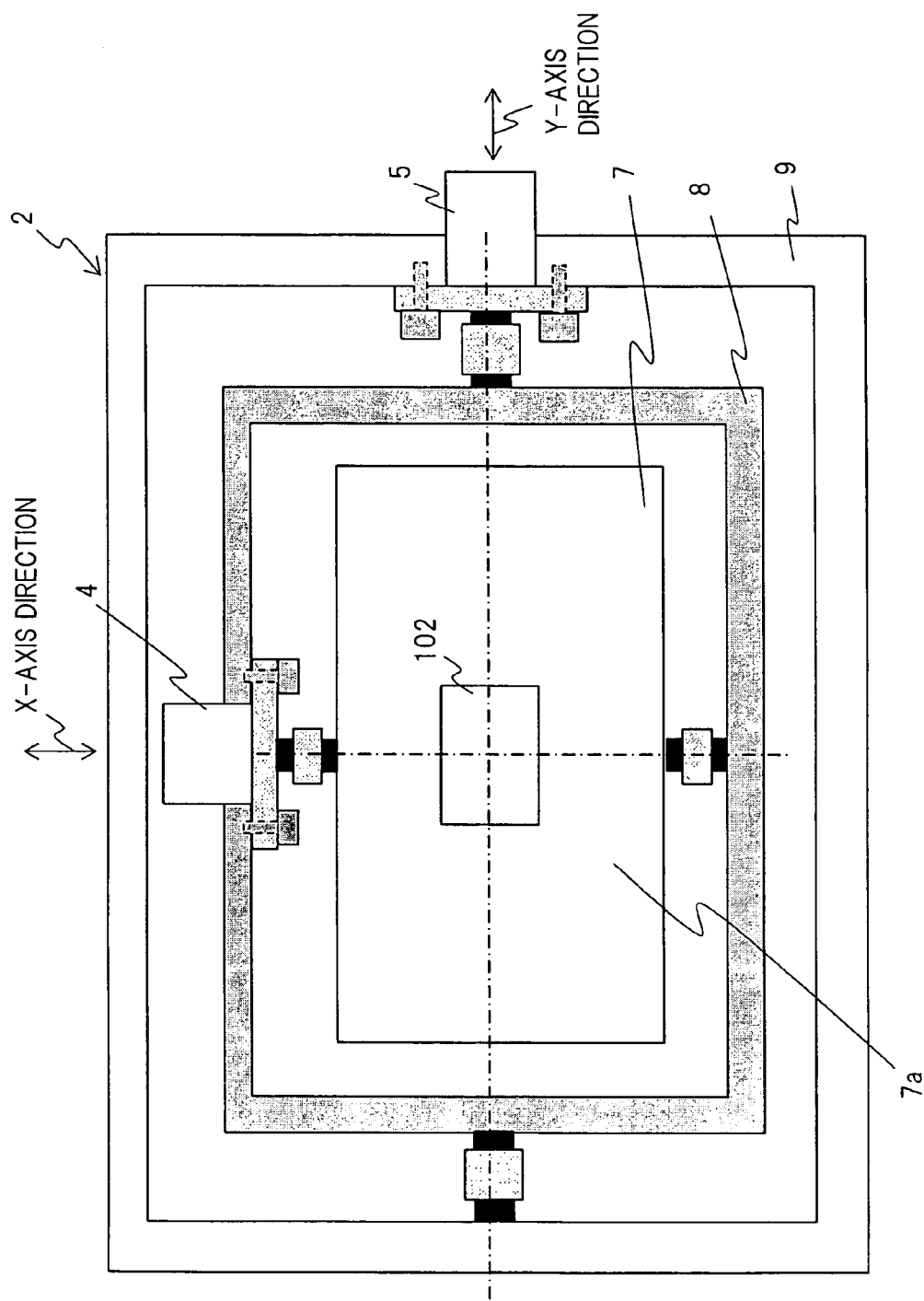
FIG. 2 is a configuration view showing a swinging mechanism in the X-ray inspection device in accordance with the first embodiment.

FIG. 2 is a plan view showing a schematic configuration of the swinging device 2 in the first embodiment. The swinging device 2 has an XY stage 7 as a moving mechanism for object to be inspected that holds the above-mentioned circuit forming body as the object to be inspected 102, an inner frame 8 to which an X-axis motor 4 that rotates the XY stage 7 around the X axis is fixed and an outer frame 9 to which a Y-axis motor 5 that rotates the XY stage 7 around the Y axis is fixed. The XY stage 7 is connected to the inner frame 8 via a coupling so as to rotate around the X axis. The inner frame 8 is connected to the outer frame 9 via a coupling so as to rotate around the Y axis. In the state shown in FIG. 2, the longitudinal direction of the XY stage 7 indicates the X-axis direction indicates the Y-axis direction.

Figure 3:
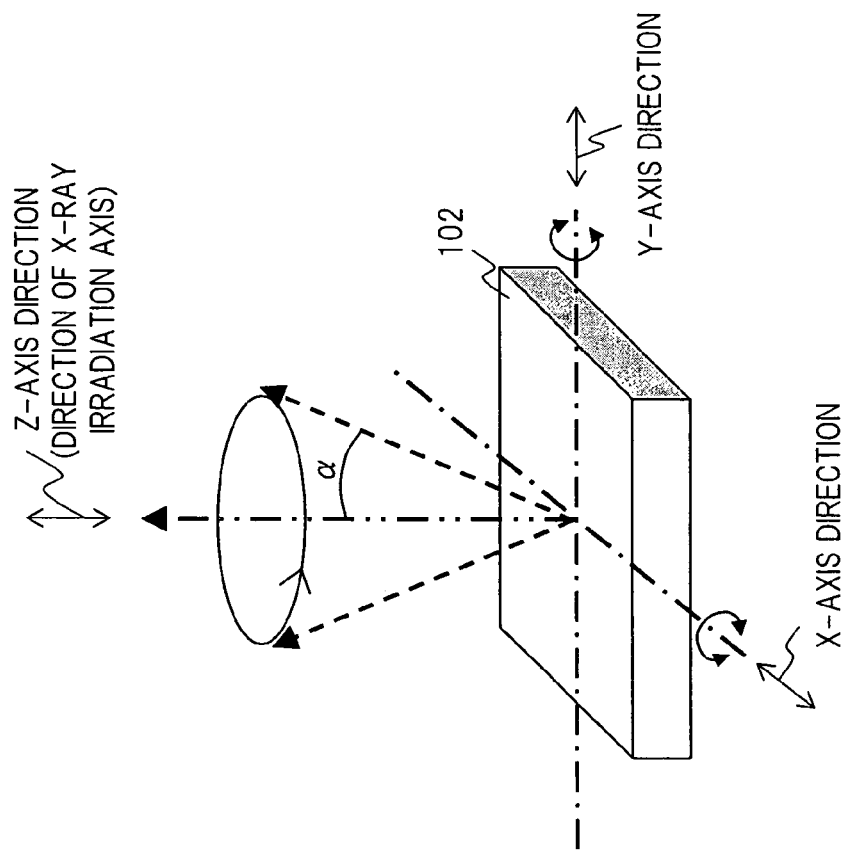
FIG. 3 is a view showing a swinging condition of an object to be inspected in the X-ray inspection device in accordance with the first embodiment.
Figure 4:
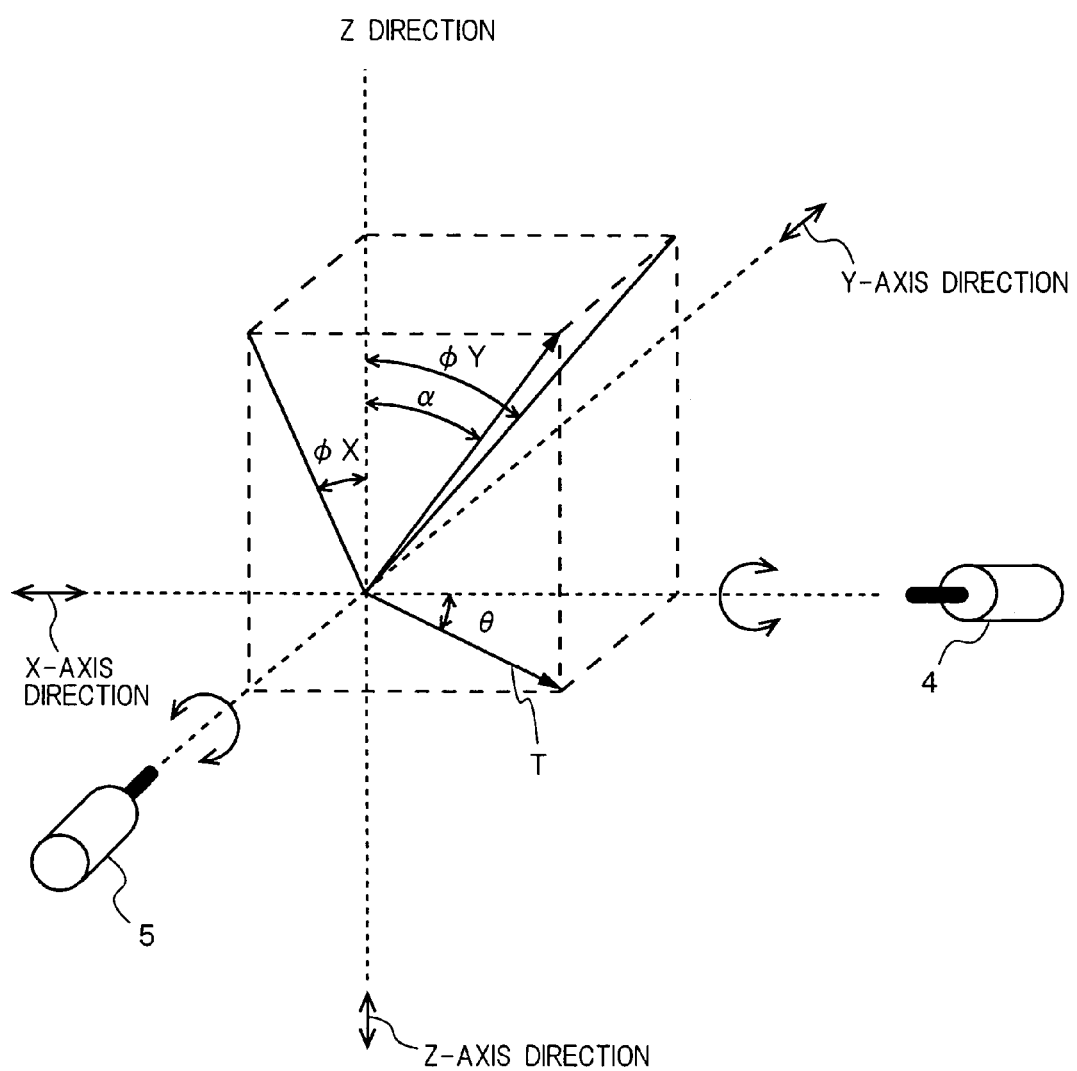
FIG. 4 is a view showing a tilt direction and a tilt angle of the object to be inspected in the X-ray inspection device in accordance with the first embodiment.

Next, the swinging condition of the object to be inspected 102 driven by the swinging device 2 of the first embodiment will be described. FIG. 3 is an explanation view illustrating a swinging condition of the object to be inspected 102 in the X-ray inspection device in accordance with the first embodiment. FIG. 4 is a conceptual diagram showing a tilt direction T and a tilt angle α of the object to be inspected 102 in the X-ray inspection device in accordance with the first embodiment.

As shown in FIG. 3, the object to be inspected 102 performs swinging motion by the swinging device 2 of the first embodiment. Here, the swinging motion means that a normal line to a central point of a holding plane 7a of the XY stage 7 that holds the object to be inspected 102 rotates around the center of the holding plane 7a as a rotation center point (swinging center point) at a predetermined angle with respect to the X-ray irradiation axis. In the first embodiment, the X-ray irradiation device 3 is located on a direct extension of the center of the swinging device 2 and the imaging center of the X-ray detection device 1 and the extension line is the X-ray irradiation axis, that is, a Z axis. Accordingly, the normal line to the center point (swinging center point) of the holding plane 7a of the XY stage 7 swings with respect to the Z axis at the predetermined angle. The swinging center point is located at an intersection of rotational axes of the X-axis motor 4 and the Y-axis motor 5 fixedly. However, by changing the position of the object to be inspected 102 on the XY stage 7, the object to be inspected 102 at any desired position can be inspected.

FIG. 4 is a conceptual diagram showing a tilt direction T and a tilt angle α of the object to be inspected 102 in the X-ray inspection device in accordance with the first embodiment. Here, the tilt direction T refers to a direction with an angle θ that the normal line to the center point of the object to be inspected 102 (central point of a holding plane 7a) forms with the X axis on the holding plane (XY plane) 7a of the XY stage 7. The tilt angle α refers to an angle that the normal line to the center point of the object to be inspected 102 forms with the Z axis. In FIG. 4, an angle φX indicates a rotation angle of the rotation axis of the X-axis motor 4 and an angle with respect to the Z axis on the YZ plane. An angle φY indicates a rotation angle of the rotation axis of the Y-axis motor 5 and an angle with respect to the Z axis on the ZX plane.

As shown in the following equation (1), the angle θ defining the tilt direction T is represented by the rotation angle φX of the X-axis motor 4 and the rotation angle φY of the Y-axis motor 5. As shown in the following equation (2), the tilt angle α is represented by the rotation angle φX of the X-axis motor 4 and the rotation angle φY of the Y-axis motor 5.

$$TAN(\theta) = TAN(\phi X)/TAN(\phi Y) \quad (1)$$

$$TAN^2(\alpha) = TAN^2(\phi X) + TAN^2(\phi Y) \quad (2)$$

As described above, by defining the rotation angle φX of the X-axis motor 4 and the rotation angle φY of the Y-axis motor 5, any tilt direction T and any tilt angle α can be set.

Figure 5:
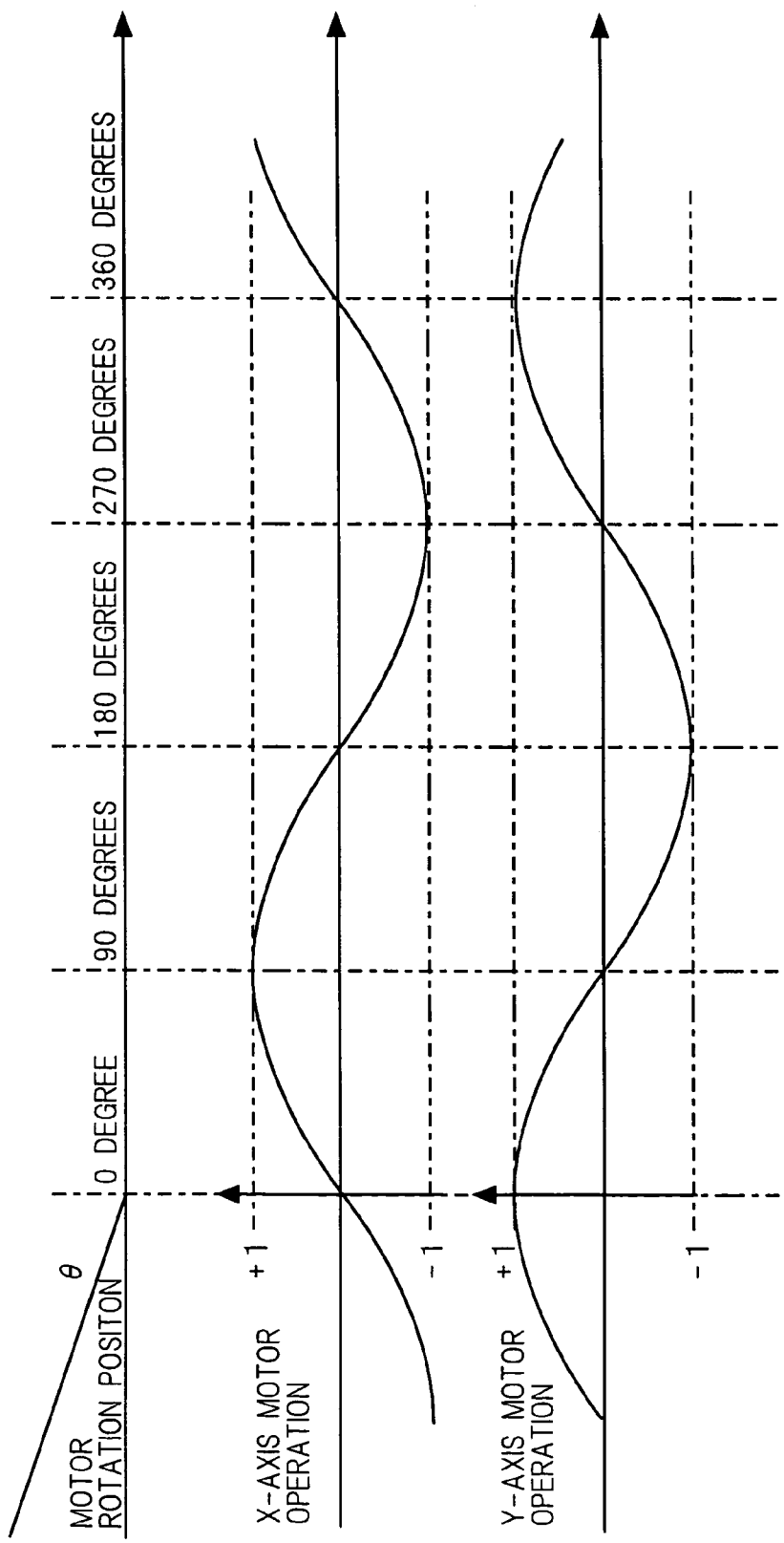
FIG. 5 is a waveform diagram showing a driving condition of an X-axis motor and a Y-axis motor in the X-ray inspection device in accordance with the first embodiment.

In the first embodiment, by defining the rotation angle φX of the X-axis motor 4 and the rotation angle φY of the Y-axis motor 5, the swinging motion with respect to the holding plane (XY plane) 7a of the XY stage 7, that is, the object to be inspected 102 is performed. FIG. 5 is a waveform diagram showing a driving operation of the X-axis motor 4 and the Y-axis motor 5 in the X-ray inspection device of the first embodiment. FIG. 5 shows the case of the tilt angle α of 45 degrees and in this case, TAN45 degrees equals to one (TAN45°=1) and maximum values of TANφX and TANφY become one.

In the first embodiment, the tilt angle α is set as 45 degrees and the angle defining the tilt direction T is varied from zero degree to 360 degrees. In this case, the X-axis motor 4 performs reciprocating motion within the range of predetermined angles and the Y-axis motor 5 operates reciprocating motion with the phase being shifted from the X-axis motor 4 as shown in FIG. 5. For example, the Y-axis motor 5 may perform reciprocating motion with the same amplitude and cycle as the X-axis motor 4 with 90 degrees phase shift.

In the above-mentioned swinging motion, when the tilt angle α is changed, the amplitude of TANφX and TAN φY changes. In the first embodiment, the tilt angle α is configured so as to be set within the range from zero degree to 75 degrees. However, it is possible to obtain a relatively good image within the range from 30 degrees to 75 degrees.

In the first embodiment, as described above, the object to be inspected 102 performs a predetermined swinging motion by the swinging device 2, and when the object to be inspected 102 reaches a predetermined position through the swinging motion, the X-ray is radiated from the X-ray irradiation device 3 and the X-ray that passes through the object to be inspected 102 is captured in the X-ray detection device 1. At this time, the control device 6 allows the X-ray detection device 1 to take an image plural times while the swinging device 2 varies the tilt direction T by 360 degrees, that is, while the swinging motion performs one rotation, and prepares and displays X-ray tomographic images.

Figure 18:
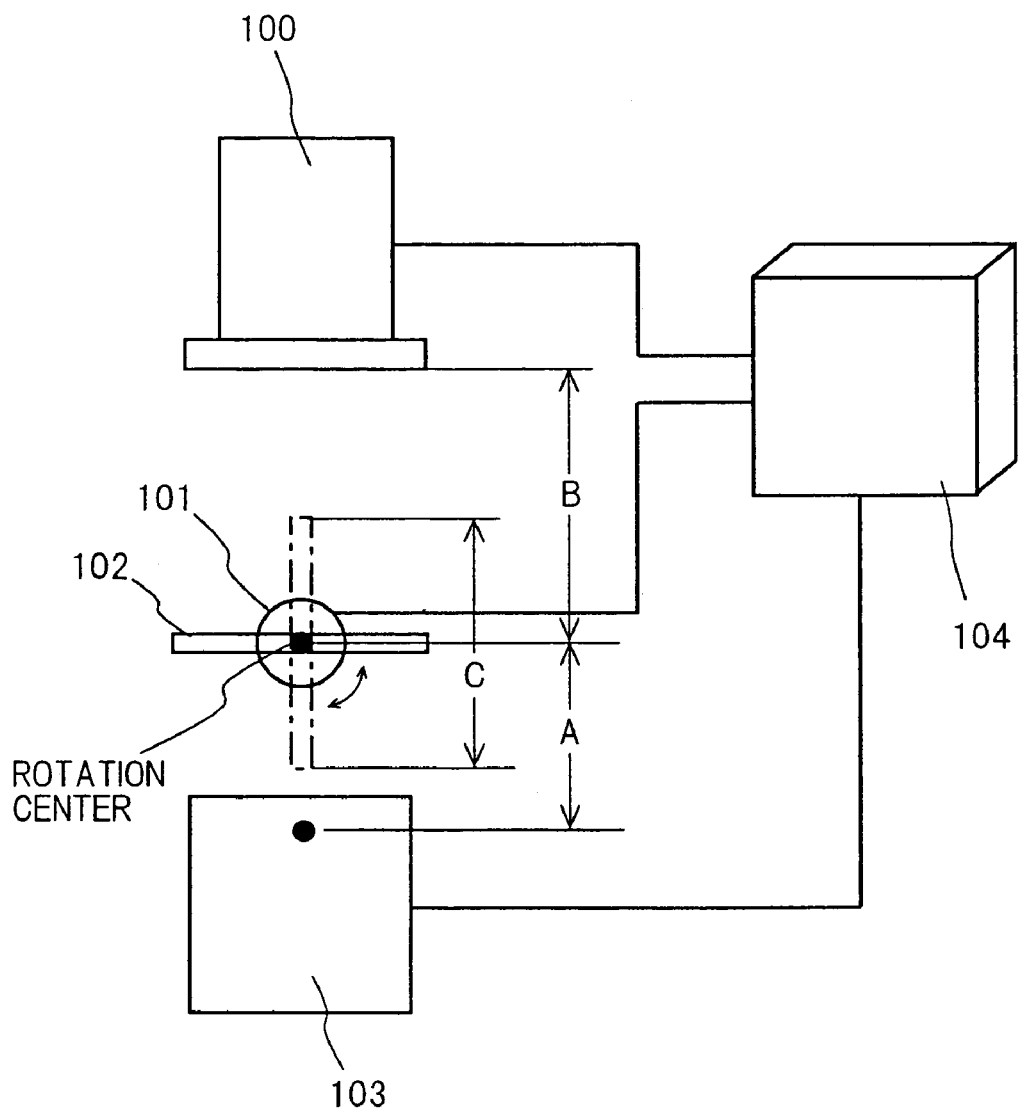
FIG. 18 is the block diagram showing a schematic configuration of a conventional X-ray inspection device by using tomography.
Figure 19:
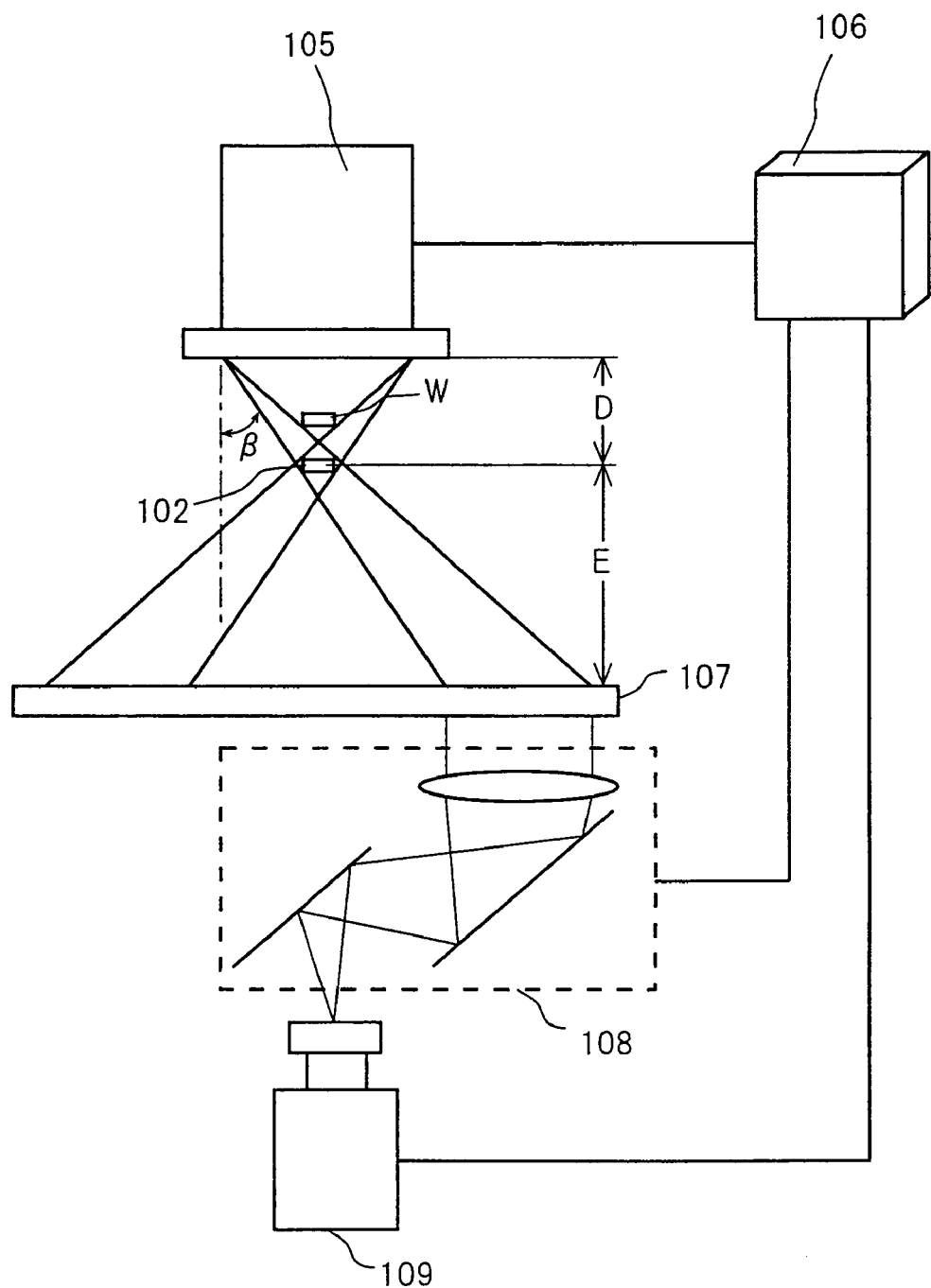
FIG. 19 is the block diagram showing a schematic configuration of the conventional X-ray inspection device by using laminography.
Figure 20:
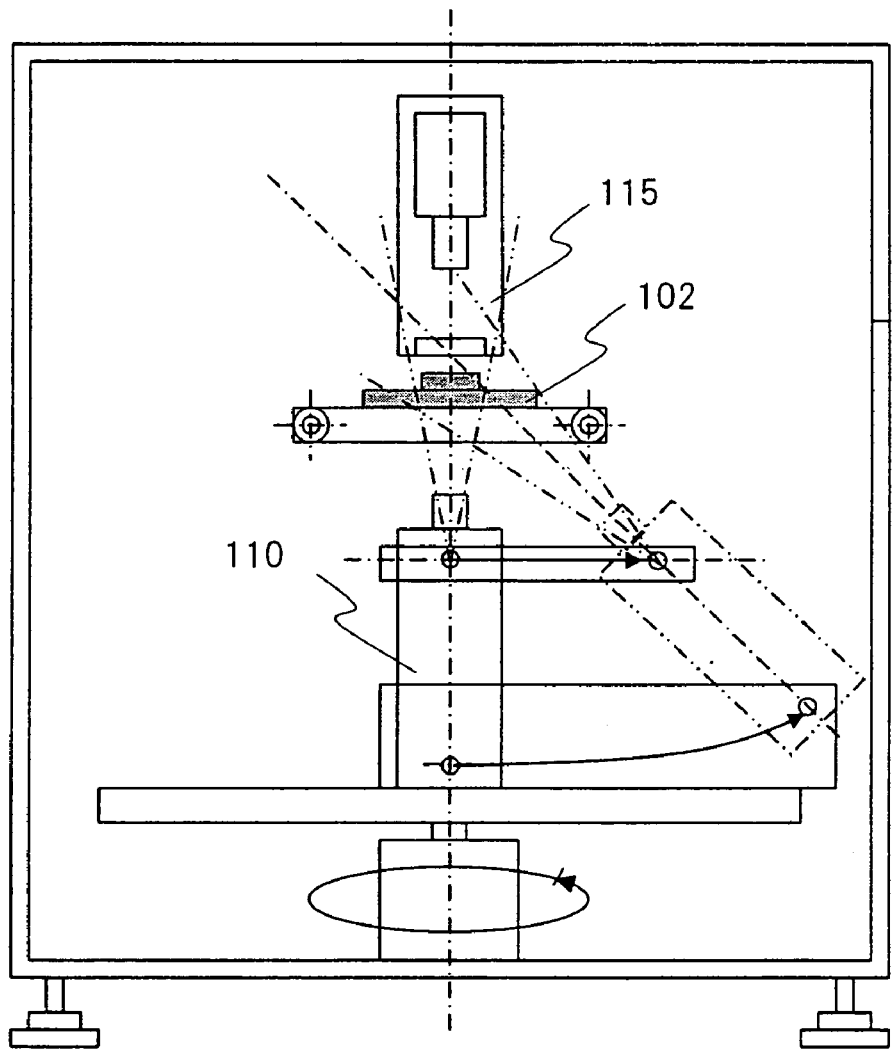
FIG. 20 is the view showing another configuration of the conventional X-ray inspection device.
Figure 21:
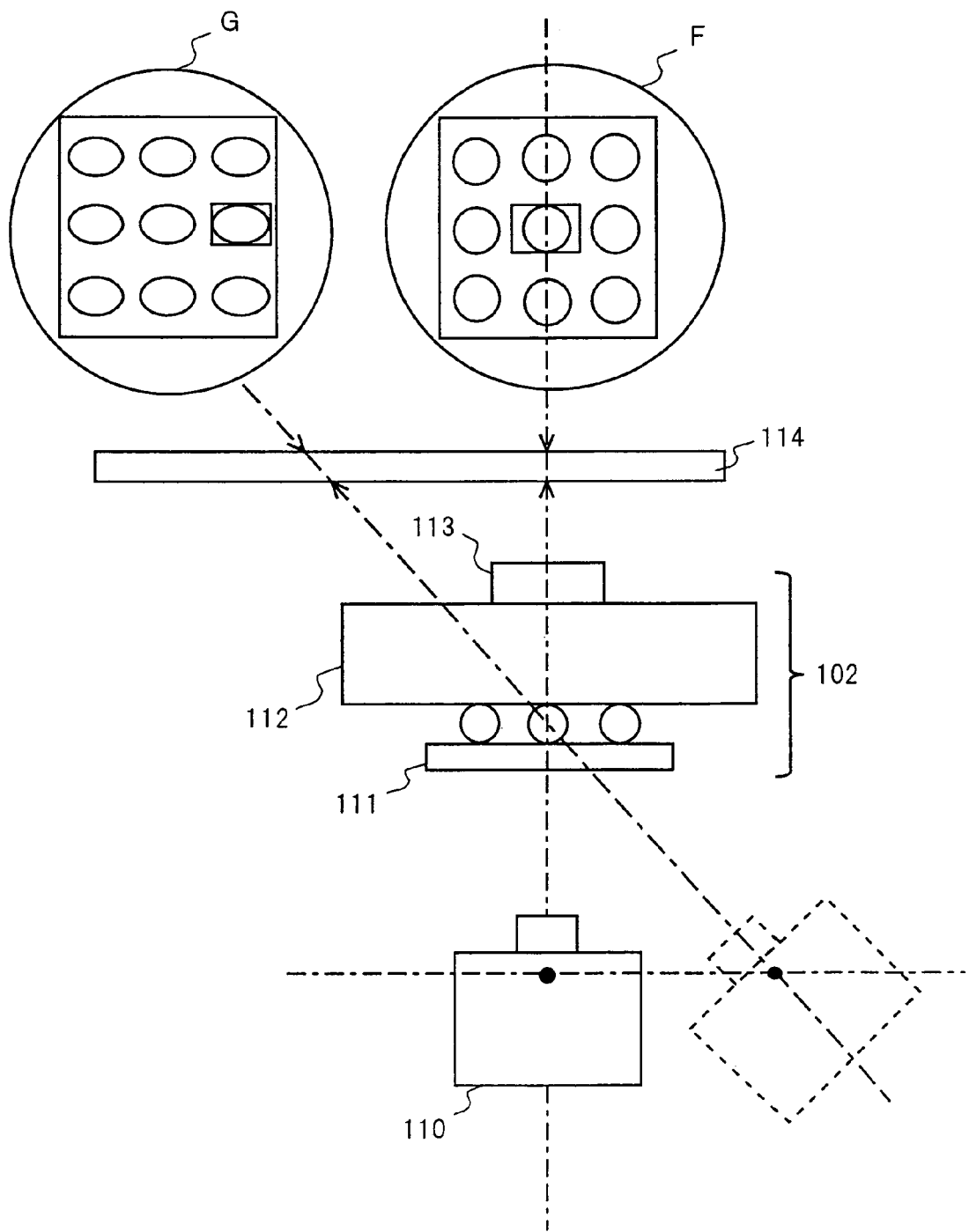
FIG. 21 is the block diagram showing a configuration and operation of a main part of the conventional X-ray inspection device shown in FIG. 20.

Since the X-ray inspection device of the first embodiment is configured so that the object to be inspected 102 performs swinging motion, the object to be inspected 102 can be moved closer to the X-ray focus (spot position) of the X-ray source without the need to rotate whole of the object to be inspected 102 by 360 degrees as in the conventional X-ray inspection device using tomography shown in FIG. 18. As a result, the X-ray inspection device of the first embodiment is a compact device with high resolution.

In the X-ray inspection device of the first embodiment, a physical fixing means such as screws is used as a means of holding the object to be inspected 102 on the XY stage 7 of the swinging device 2. In the swinging device 2, a driving mechanism comprised of a rack and a pinion is provided so that whole of the swinging device 2 is arbitrary moved in the direction of X-ray irradiation axis (Z-axis direction). A driving mechanism may be also provided at the X-ray detection device 1 and the X-ray irradiation device 3 so that the X-ray detection device 1 and the X-ray irradiation device 3 can be moved in the direction of X-ray irradiation axis (Z-axis direction) simultaneously or separately, thereby enabling to set the magnifying factor of the X-ray image greater.

The X-ray detection device 1 of the first embodiment has the function of converting dose of the X-ray into an electrical signal. The X-ray detection device 1 is provided with a scintillator for converting the X-ray into visible light and after the conversion of the incident X-ray into visible light by the scintillator, the light is converged by a lens and entered into a photoelectric converter element such as CCD and CMOS. Therefore, in the first embodiment, it is configured so that the resolution of the X-ray is determined by the scintillator and the lens and then the dose of the X-ray is converted into an electrical signal.

Another X-ray detection device may have the following configuration and operations. Similarly to an X-ray image intensifier, the incident X-ray is converted into a charged particle by a first scintillator for converting the X-ray into the charged particle and the charged particle is converged by magnetic field control. Subsequently, the converged charged particle is converted into light by a second scintillator for converting the charged particle into visible light and the light is converted into an electrical signal by using a photoelectric converter element such as CCD and CMOS. Alternatively, it is possible that, like an X-ray flat panel, the X-ray is converted into light by a scintillator for converting the X-ray into visible light and then the light is directly entered into the photoelectric converter element such as CCD and CMOS and converted into an electrical signal.

In the first embodiment, the control device 6 performs ON/OFF control of irradiation of the X-ray by the X-ray irradiation device 3, setting of X-ray tube voltage, setting of X-ray tube current and monitoring of error and controls the tilt direction T and the tilt angle α of the swinging device 2. The control device 6 also performs an arithmetical operation of the electrical signal as the X-ray image data input from the X-ray detection device 1 and displays the state of the operated electrical signal. The control device 6 has the function of displaying tomographic data from a plurality of X-ray images by means of tomography. The inspection method in the control device 6 includes a method in which a tilted image obtained by the X-ray detection device 1 is displayed as it is and judged by the operator and a method in which a three dimensional image is created from a plurality of X-ray images by means of tomography, and an arbitrary cross section from the stereoscopic image is displayed and judged by the operator.

Figure 6:
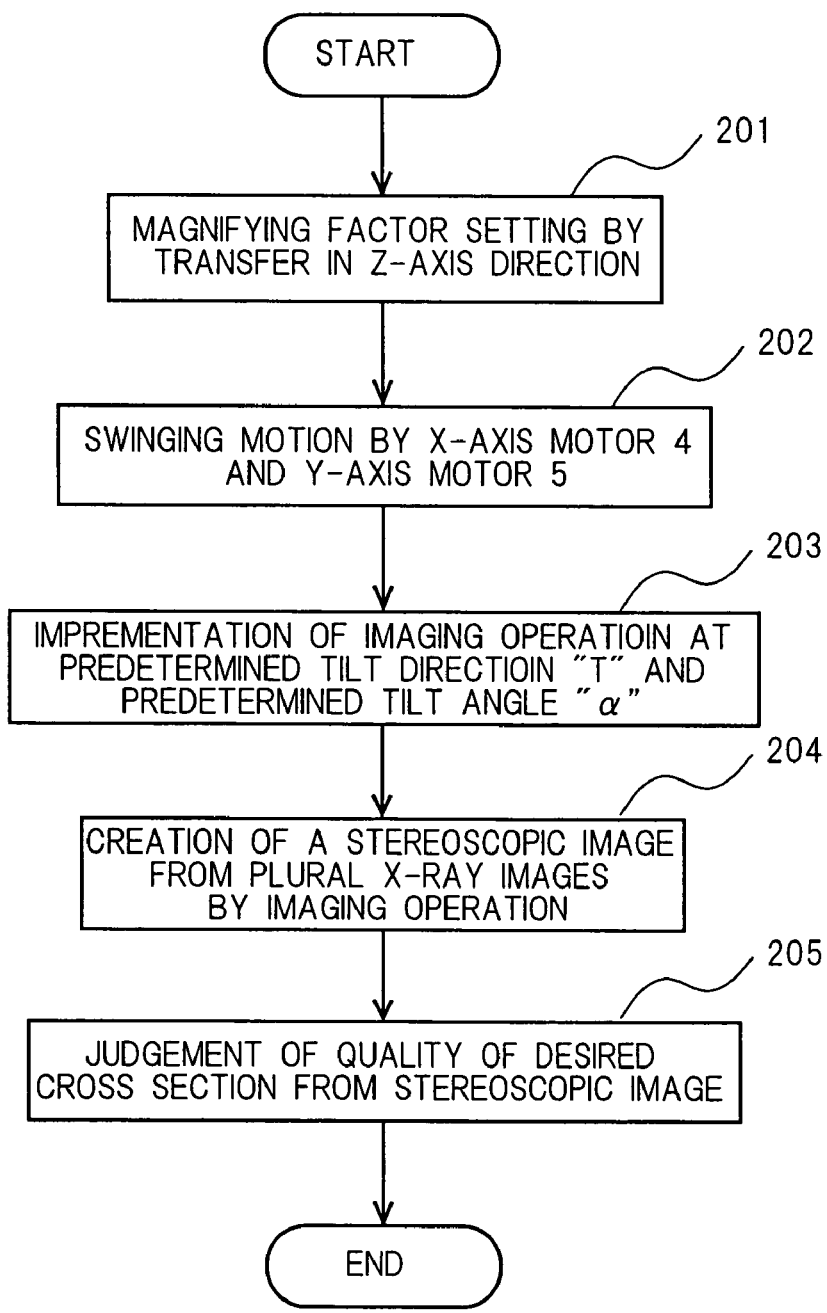
FIG. 6 is a flowchart showing an operation in the X-ray inspection device in accordance with the first embodiment.

FIG. 6 is a flowchart showing the inspecting operation in the X-ray inspection device in accordance with the first embodiment.

As shown in FIG. 6, in the X-ray inspection device in accordance with the first embodiment, firstly at a step 201, the swinging device 2 is transferred in the Z-axis direction (direction of X-ray irradiation axis) so as to set a desired magnifying factor. Next, at a step 202, the XY stage 7 to which the object to be inspected 102 is fixed is swung by rotating the X-axis motor 4 and the Y-axis motor 5. During the swinging motion, when the holding plane 7a of the XY stage 7 reaches a predetermined tilt direction T and a predetermined tilt angle α, the imaging operation in which the X-ray is irradiated from the X-ray irradiation device 3 and the X-ray image that passes through the object to be inspected 102 is captured in the X-ray detection device 1 is performed (step 203). This imaging operation is performed at predetermined plural positions. In other words, while the tilt direction T of the holding plane 7a varies by 360 degrees (during one rotation), an image is taken by the X-ray detection device 1 plural times to obtain a predetermined number of X-ray images. A stereoscopic image (three-dimensional image) of the object to be inspected 102 is created from the obtained plural X-ray images and displayed on a display part of the control device 6 (step 204). The state of a desired cross section is detected from the created stereoscopic image to check the quality (step 205). In the quality check, a difference between pre-acquired data on the cross section in good condition and data on the cross section of the object to be inspected 102 is obtained and inspection may be conducted based on the difference image.

As described above, with compact and inexpensive configuration, the X-ray inspection device in accordance with the first embodiment can obtain the X-ray image of the object to be inspected 102 at any tilt direction and tilt angle with high precision as well as obtain the tomographic image with less blur and false echo by finding the tomographic image from a plurality of tilted images by calculation in the control device 6. Further, since tomographic data on a printed circuit board with high packaging density or a thin board can be obtained reliably, the inspection using a clear tomographic image having high resolution becomes possible.

Figure 7:
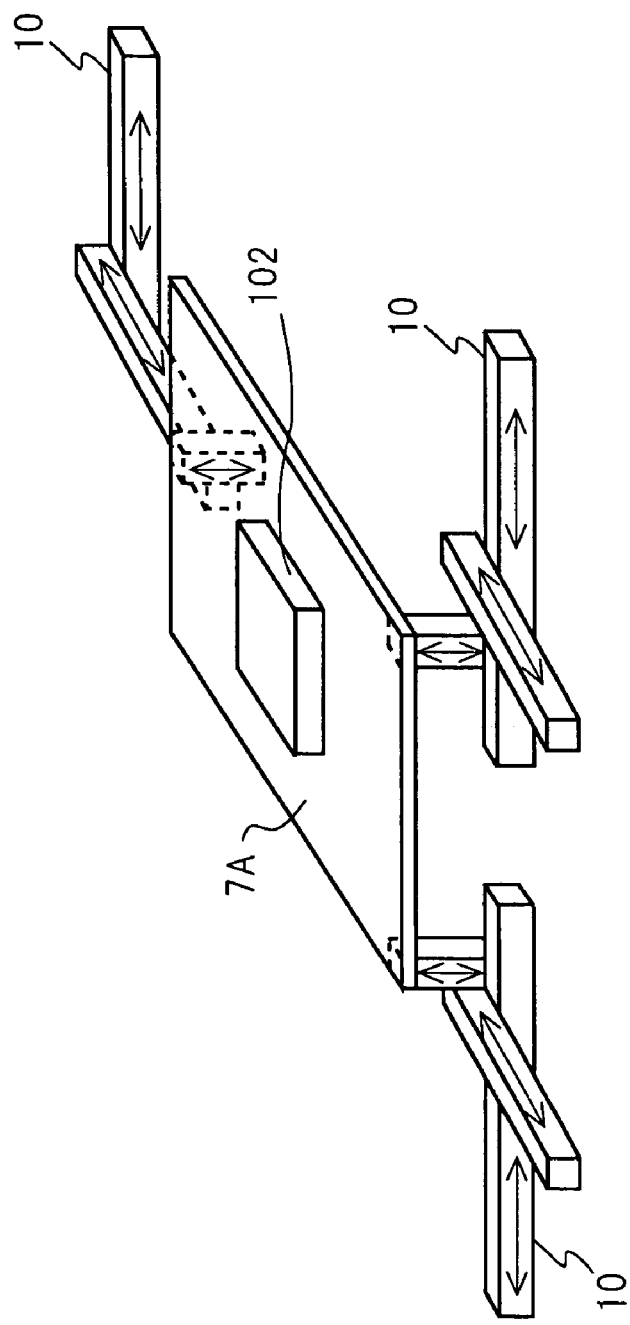
FIG. 7 is a view showing another configuration of the swinging mechanism in the X-ray inspection device of the present invention.
Figure 8:
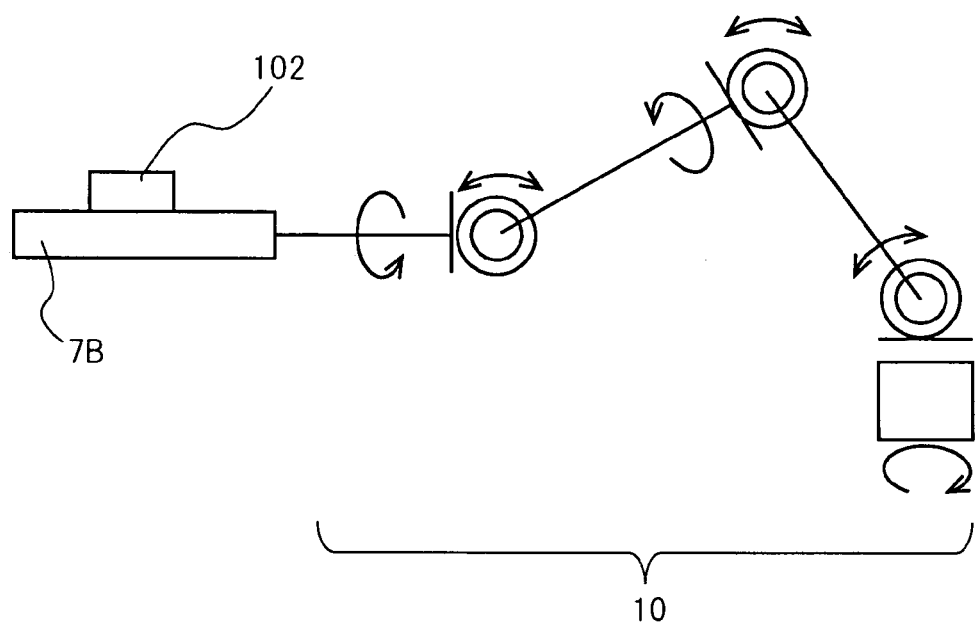
FIG. 8 is a view showing further another configuration of the swinging mechanism in the X-ray inspection device of the present invention.

In the first embodiment, while the example in which the swinging mechanism using the X-axis motor 4 and the Y-axis motor 5 is employed as the swinging device 2 is described, it is possible to use multi-axial control devices 10 having three or more axes. FIG. 7 is a modification of the swinging device 2 of the first embodiment and a stage 7A to which the object to be inspected 102 is fixed is driven by the three multi-axial control devices 10. Each of the multi-axial control devices 10 is configured so as to transfer the stage 7A in the X-axis direction, the Y-axis direction and the Z-axis direction. FIG. 8 is further another modification of the swinging device 2. In the swinging device 2 shown in FIG. 8, a stage 7B to which the object to be inspected 102 is fixed is driven by a multi-axial control device 10 as a six-axis robot. Accordingly, the stage 7B can perform the swinging motion and sliding motion of the object to be inspected 102 in the X-axis, Y-axis and Z-axis directions by using an arm of the six-axis robot. As shown in FIG. 7 or FIG. 8, with a multi-axial control mechanism 301, the stage 7A or 7B to which the object to be inspected 102 is fixed is swung and the swinging motion and sliding motion in the X-axis, Y-axis and Z-axis directions are performed. This enables the object to be inspected 102 to perform a desired operation, thereby enabling to easily carry out the function of changing in inspection position or magnifying factor.

<<Second Embodiment>>

Figure 9:
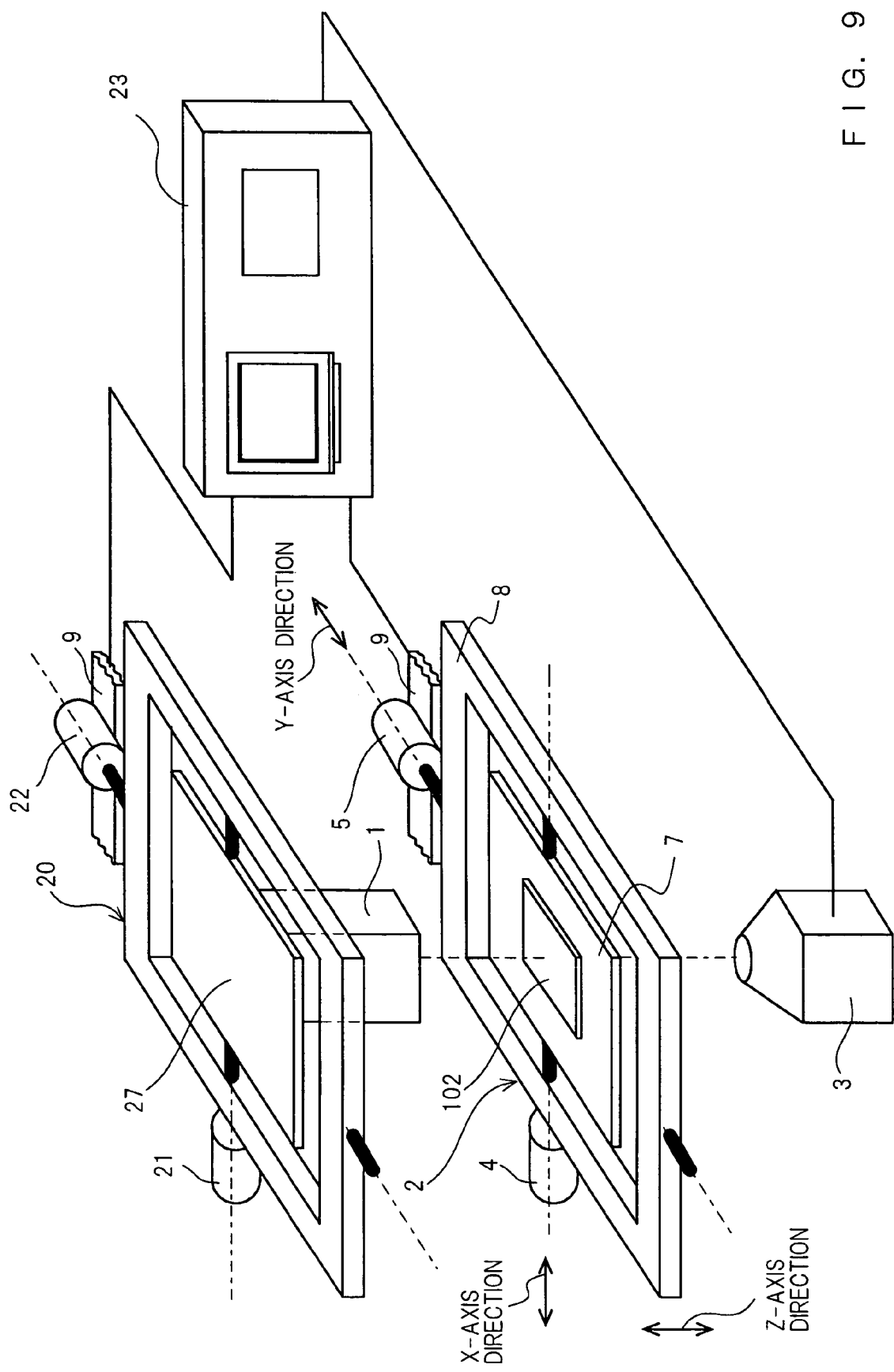
FIG. 9 is a view showing a schematic configuration of an X-ray inspection device in accordance with a second embodiment of the present invention.
Figure 10:
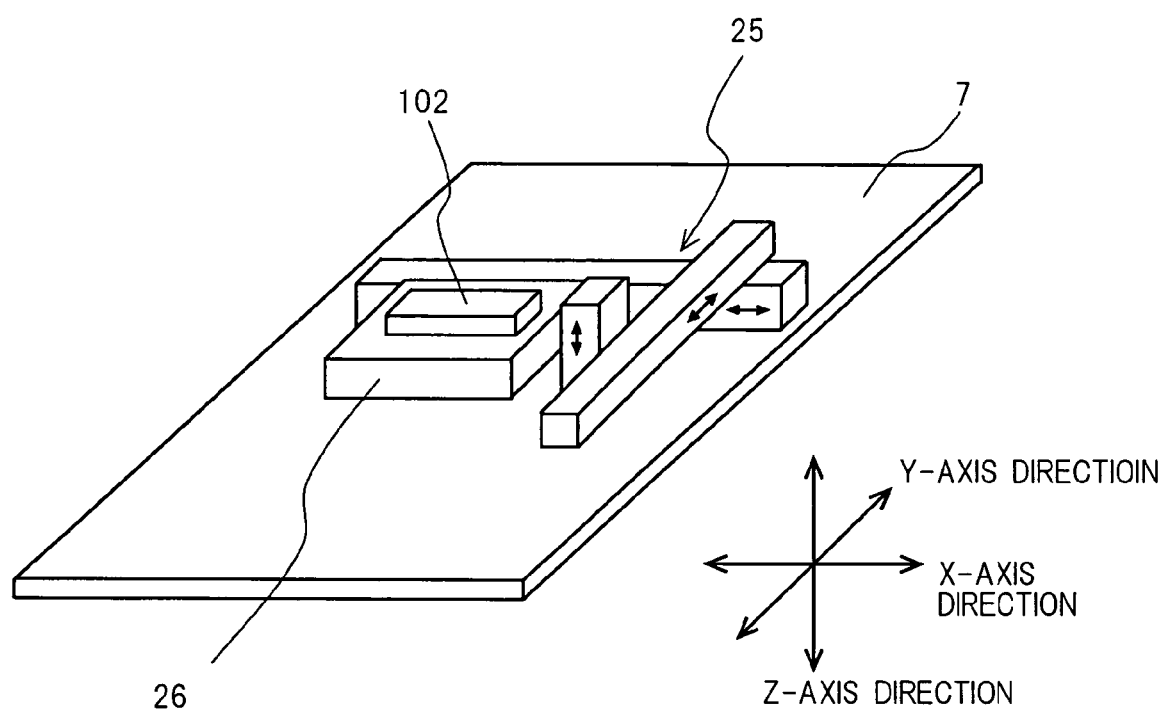
FIG. 10 is a configuration view showing a driving mechanism for an object to be inspected in the X-ray inspection device in accordance with the second embodiment.

FIG. 9 is a view showing a schematic configuration of an X-ray inspection device in accordance with a second embodiment of the present invention. FIG. 10 is a configuration view showing a driving mechanism of the object to be inspected in the X-ray inspection device of the second embodiment. The X-ray inspection device of the second embodiment has a swinging device 20 for X-ray detection for swinging the X-ray detection device 1 in addition to the above-mentioned swinging device 2 of the X-ray detection device 1 of the first embodiment and an XYZ transfer table 26 capable of transferring in the X-axis, Y-axis and Z-axis directions. The same reference numerals are given to elements of the second embodiment having the same function and configuration as those of the first embodiment and description thereof is omitted.

As shown in FIG. 9, also in the X-ray inspection device of the second embodiment, the X-ray radiated from the X-ray irradiated device 3 is irradiated to the object to be inspected 102 held by the swinging device 2 and the X-ray that passes through the object to be inspected 102 is detected by the X-ray detection device 1. The X-ray focus (spot position) of the X-ray irradiation device 3 is located on the direct extension of the center of the swinging device 2 and the imaging center position of the X-ray detection device 1 and emits the X-ray toward the X-ray detection device 1.

In the X-ray inspection device of the second embodiment, as shown in FIG. 10, a multi-axial control device 25 as a driving mechanism of the object to be inspected is provided on the XY stage 7 of the swinging device 2. This multi-axial control device 25 is not shown in FIG. 9. In the X-ray inspection device of the second embodiment, the XVZ transfer table 26 on the XY stage 7 is configured so as to be movable in the X-axis, Y-axis and Z-axis directions by the multi-axial control device 25. The circuit forming body such as a printed circuit board and electronic components as the object to be inspected 102 is fixed on the XVZ transfer table 26.

In the X-ray inspection device of the second embodiment, a swinging device 20 for X-ray detection for swinging the X-ray detection device 1 is provided. Like the swinging device 2, the swinging device 20 for X-ray detection for swinging the object to be inspected 102 has an XY stage 27 to which the X-ray detection device 1 is fixed, an X-axis motor 21 for rotating the XY stage 27 around the X axis, and a Y-axis motor 22 for rotating the XY stage 27 around the Y axis. However, the XY stage 27 does not move in the Z-axis direction. The swinging device 20 for X-ray detection of the second embodiment is driven in the same direction as the swinging device 2 in synchronization with the swinging device 2. That is, the XY stage 27 of the swinging device 20 for X-ray detection and the XY stage 7 of the swinging device 2 swing so as to be in the same direction at all times.

The control device 23 of the second embodiment controls transfer of the swinging device 2 in the Z-axis direction, tilt angle of the XY stage 7 with respect to the X axis and Y axis and tilt angle of the XY stage 27 of the swinging device 20 for X-ray detection with respect to the X axis and Y axis. The control device 23 also controls driving of the X-ray detection device 1 and the X-ray irradiation device 3. The control device 23 controls driving so that the X-ray is irradiated from the X-ray irradiation device 3 when the swinging device 2 that holds the object to be inspected 102 forms a predetermined angle and the X-ray that passes through the object to be inspected 102 is captured in the X-ray detection device 1. Subsequently, data of the X-ray image captured in the X-ray detection device 1 is input to the control device 23 and the X-ray image data is calculated in the control device 23 and the calculations result is displayed. It is configured that the quality of information on the cross section created in the control device 23 is judged automatically and displayed.

In the X-ray inspection device of the second embodiment, the multi-axial control device 25 and the XVZ transfer table 26 are provided on the XY stage 7 of the swinging device 2 and the XVZ transfer table 26 is configured so as to be independently transferable in the X-axis, Y-axis and Z-axis directions. This enables setting the object to be inspected 102 at an arbitrary position with respect to the XY stage 7 (position in the X-axis direction, position in the Y-axis direction and position in the Z-axis direction). Accordingly, an arbitrary part of the object to be inspected 102 can be set at predetermined tilt angle and tilt direction with respect to the reference position of X-ray irradiation on the XY stage 7. As a result, the X-ray inspection device of the second embodiment can inspect all positions of the object to be inspected 102 easily.

In the X-ray inspection device of the second embodiment, the swinging device 20 for X-ray detection for swinging the X-ray detection device 1 is provided and the swinging device 20 for X-ray detection is driven in the same direction as the swinging device 2 in synchronization with the swinging device 2. That is, the XY stage 27 of the swinging device 20 for X-ray detection and the XY stage 7 of the swinging device 2 are set to have the same tilt direction T and the same tilt angle α. As a result, the X-ray inspection device of the second embodiment can prevent distortion in the X-ray image. In the X-ray inspection device of the second embodiment, as a method of controlling both of the XY stage 27 of the swinging device 20 for X-ray detection and the XY stage 7 of the swinging device 2 in the same manner, rotation position of each motor is detected and the control device 23 performs feedback control based on the rotation position to drive these devices.

As another method of controlling the swinging device 20 for X-ray detection and the swinging device 2 in the same manner, it is possible to realize the same tilt direction T and the same tilt angle α by physically connecting to the swinging device 20 for X-ray detection with the swinging device 2 and controlling either of the swinging mechanism by motor.

In the X-ray inspection device of the second embodiment, the control 23 has a function of automatic inspection by algorithm. For this reason, the reliable and stable X-ray inspection without variation in inspection quality can be achieved.

Figure 11:
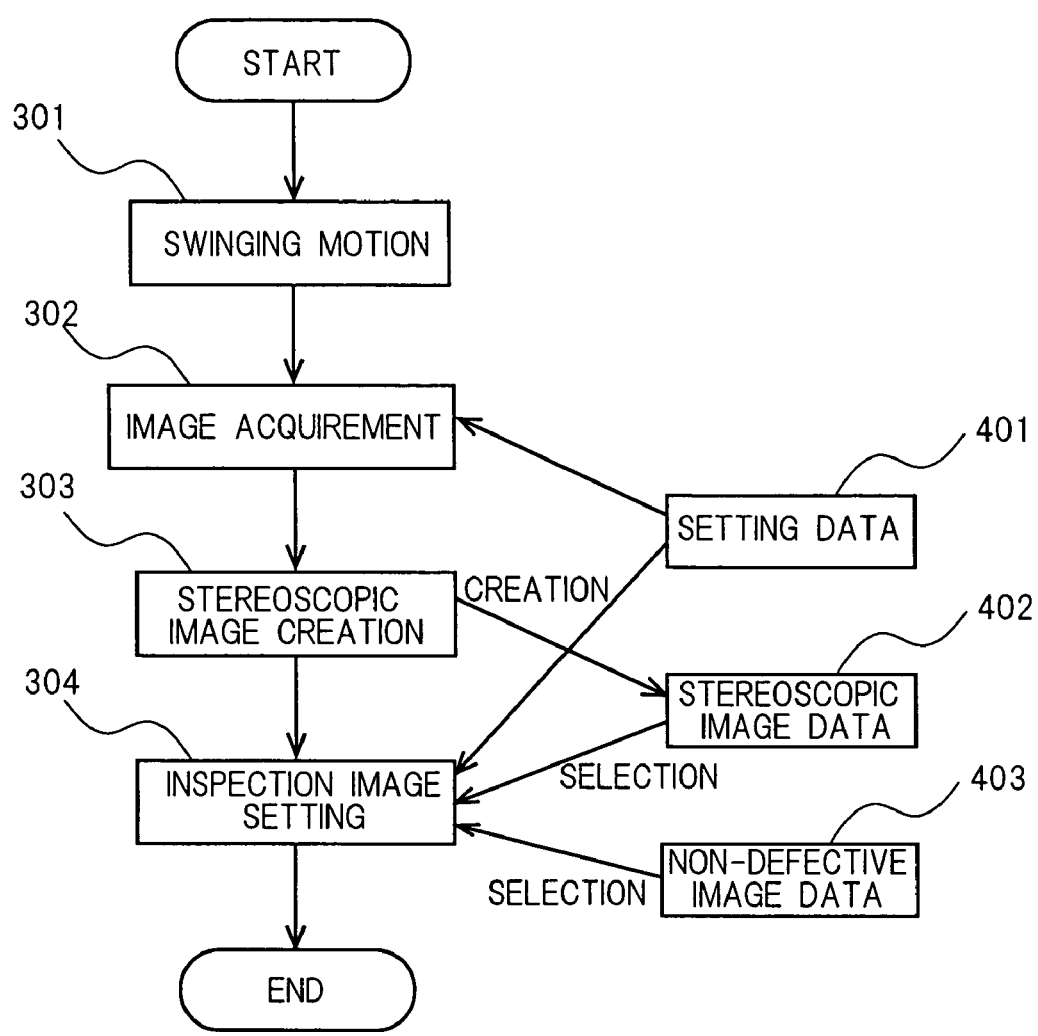
FIG. 11 is a flowchart showing an operation of the X-ray inspection device in accordance with the second embodiment.

FIG. 11 is a flowchart showing the operation of automatic inspection function by algorithm of the control device 23.

At a swinging motion step 301 in FIG. 11, the XYZ transfer table 26 is located at a desired position by the multi-axial control device 25 and the swinging device 2 is transferred in the Z-axis direction (direction of X-ray irradiation axis) so as to set a desired magnifying factor. Next, the XY stage 7 to which the object to be inspected 102 is fixed and the swinging device 20 for X-ray detection are swung in synchronization with each other. During this swinging motion, when the holding plane 7a of the XY stage 7 achieves a predetermined tilt direction T and a predetermined tilt angle α, the X-ray is irradiated from the X-ray irradiation device 3 and the X-ray that passes through the object to be inspected 102 is captured in the X-ray detection device 1. This imaging operation is performed at plural positions of predetermined tilt directions T and predetermined tilt angles α. That is, while the tilt direction T of the holding plane 7a varies by 360 degrees (during one rotation), an image is taken by the X-ray detection device 1 plural times to acquire a predetermined number of X-ray images (image acquiring step 302).

All X-ray images of each cross section in non-defective condition at predetermined tilt directions T and predetermined angles α are obtained and stored in a setting data storage part 401. Accordingly, at the image acquiring step 302, information on the tilt direction T and angle α is sent from the setting data storage part 401 to the control device 23 that controls driving of the swinging device 2 and the swinging device 20 for X-ray detection.

At a stereoscopic image creating step 303, stereoscopic image data of the object to be inspected 102 is created according to the algorithm of a stereoscopic image data storage part 402 by using tomography.

Next, at an inspection image setting step 304, a specified cross section is designated based on the information sent from the setting data storage part 401 and partial information on the created stereoscopic image data is selected. Data of the specified cross section formed by the selected information is compared with data of the cross section in the stored stereoscopic image data on non-defective condition of the object to be inspected. The stereoscopic image data on non-defective condition is selected and sent from a non-defective image data storage part 403. At the inspection image setting step 304, the quality is judged according to the correlation value in comparison based on a quality judgment reference value stored in the setting data storage part 401.

As described above, the X-ray inspection device of the second embodiment can perform X-ray inspection reliably and easily by automatic inspection function of the control device 23.

The X-ray inspection device of the second embodiment can build an automatic inspection system by using an image recognition device. In the automatic inspection system, inspection can be performed continuously by installing the X-ray inspection device in a production line and automatically conveying the circuit forming body such as a printed circuit board under production by a conveyor.

In the X-ray inspection device of the second embodiment, since the XYZ transfer table 26 is provided on the XY stage 7 of the swinging device 2, the object to be inspected 102 can be set at any position with respect to the XY stage 7 and any part of the object to be inspected 102 can be set at a predetermined tilt angle and in a predetermined direction with respect to the X-ray irradiation reference position on the XY stage 7. As a result, the X-ray inspection device of the second embodiment can create the highly detailed tomographic image with less blur and false echo from obtained X-ray image and inspect whole of the object to be inspected 102 more easily and accurately.

Further, as in a third embodiment, it may be configured that the swinging device 20 for X-ray detection and the X-ray irradiation device 3 is provided with a driving mechanism so as to transfer the swinging device 20 for X-ray detection and the X-ray irradiation device 3 in the direction of X-ray irradiation axis (Z-axis direction) simultaneously or separately, thereby enabling the magnifying factor of the X-ray image to be set greater.

<<Third Embodiment>>

Figure 12:
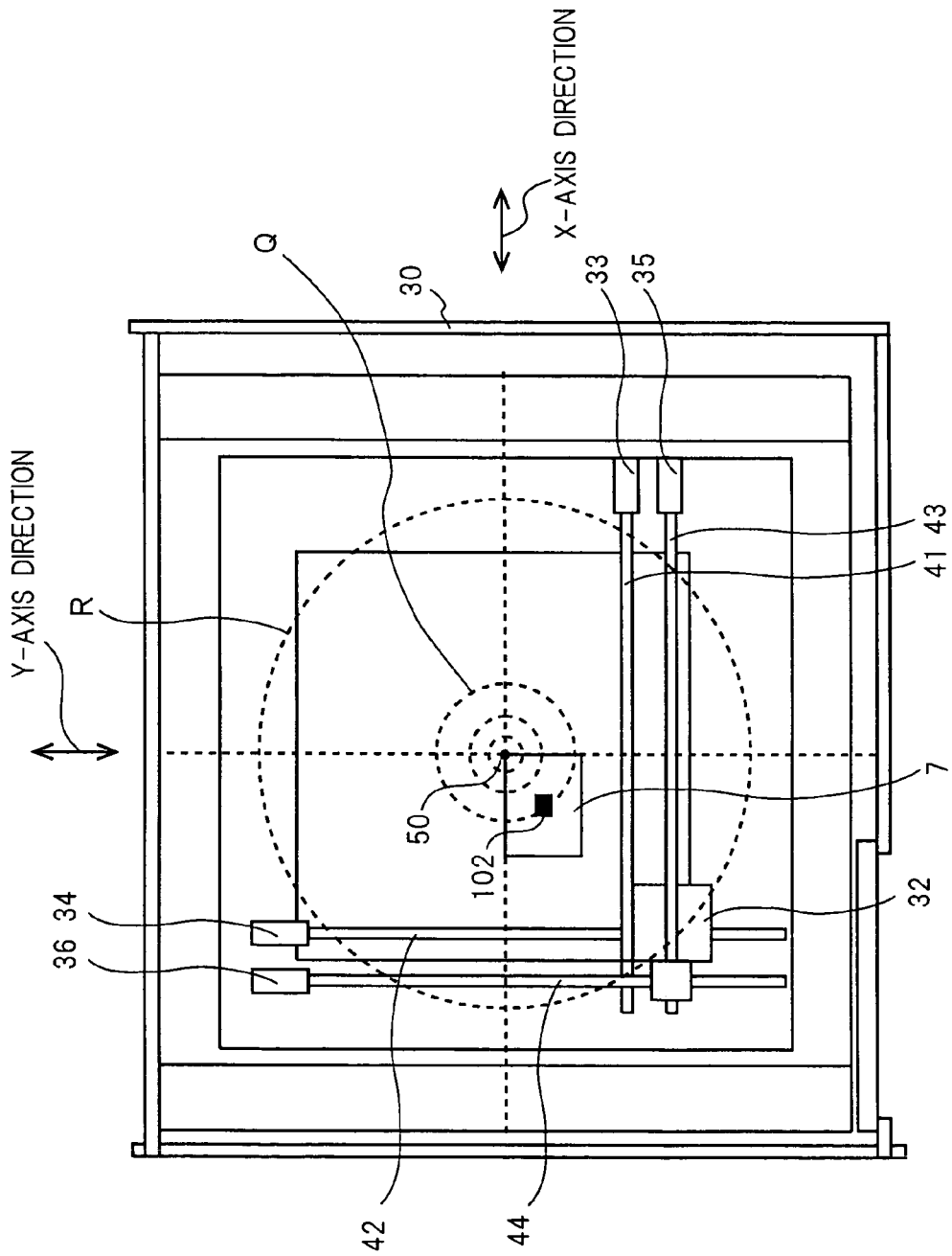
FIG. 12 is a plan cross-sectional view showing a main internal configuration of an X-ray inspection device in accordance with a third embodiment.
Figure 13:
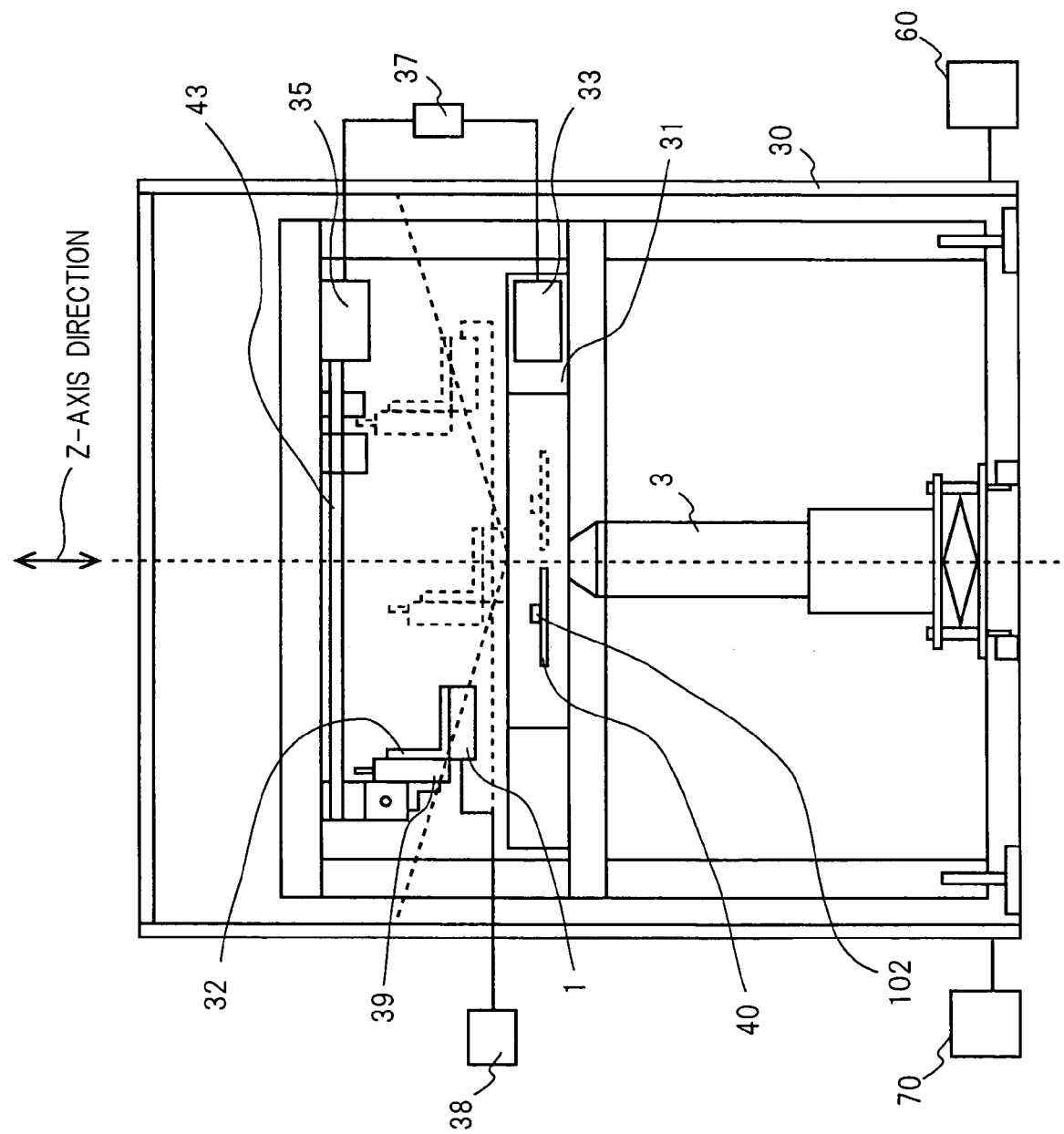
FIG. 13 is a front cross-sectional view showing a main internal configuration of the X-ray inspection device in accordance with the third embodiment.

FIG. 12 is a plan cross-sectional view showing a main internal configuration of an X-ray inspection device in accordance with a third embodiment of the present invention and FIG. 13 is a front cross-sectional view thereof. FIG. 14 to FIG. 17 are explanation views of radiography and image synthesis in the X-ray inspection device in accordance with the third embodiment. The same reference numerals are given to elements of the third embodiment having the same function and configuration as those of the first and second embodiments and description thereof is omitted.

In FIG. 12 and FIG. 13, the X-ray detection device 1, the X-ray irradiation device 3, an XY stage 31 for board as a transfer mechanism for object to be inspected and an XY stage 32 for X-ray detection as a transfer mechanism for X-ray detection are arranged in an X-ray shield box 30. Aboard holding mechanism 40 to which a printed circuit board and so on as the object to be inspected 102 is attached on the XY stage 31 for board formed directly above the X-ray irradiation device 3. The board holding mechanism 40 is configured so as to be transferable in the X-axis direction and the Y-axis direction with respect to the XY stage 31 for board. The XY stage 31 for board is provided with an X-axis driving mechanism 41 for board having an X-axis motor 33 for board and a Y-axis driving mechanism 42 for board having a Y-axis motor 34 for board. The board holding mechanism 40 is driven in the X-axis direction and the Y-axis direction by the X-axis driving mechanism 41 for board and the Y-axis driving mechanism 42 for board.

The X-ray detection device 1 is fixed to the XY stage 32 for X-ray detection. The XY stage 32 for X-ray detection is provided with an X-axis driving mechanism 43 for X-ray detection having an X-axis motor 35 for X-ray detection and a Y-axis driving mechanism 44 for X-ray detection having a Y-axis motor 36 for X-ray detection. Accordingly, the XY stage 32 for X-ray detection to which the X-ray detection device 1 is fixed is configured so as to be transferable in the X-axis direction and the Y-axis direction. Further, the XY stage 32 for X-ray detection is provided with a Z-axis driving mechanism 39 for X-ray detection so as to be transferable in the Z-axis direction (vertical direction in FIG. 13).

A motor control device 37 (indicated by a block in FIG. 13) controls each of the motors for driving the XY stage 31 for board and the XY stage 32 for X-ray detection simultaneously. A display device 38 (indicated by a block in FIG. 13) displays X-ray image data from the X-ray detection device 1 and calculated X-ray tomographic image data.

In the X-ray inspection device of the third embodiment, the X-ray irradiation device 3 is fixed to a lower part within the X-ray shield box 30. The X-ray is radially irradiated upwards from an X-ray focus (X-ray spot) 50 of the X-ray irradiation device 3 with a large irradiation angle. The X-ray radiated from the X-ray focus 50 passes through the object to be inspected 102, for example, a printed circuit board and enters into the X-ray detection device 1. When the X-ray passes through the object to be inspected 102, the X-ray attenuates depending on X-ray absorption ratio of the material of the object to be inspected 102. In the X-ray detection device 1, the X-ray image is created by converting into a gray image in proportion to the intensity of the captured X-ray. The created X-ray image is displayed on a display device 38.

In the X-ray inspection device of the third embodiment, the object to be inspected 102 is secured by the board holding mechanism 40 of the XY stage 31 for board so as to be transferable in the X-axis direction and the Y-axis direction. The object to be inspected 102 can transfer any position on the horizontal plane of the XY stage 31 for board by the X-axis driving mechanism 41 for board and the Y-axis driving mechanism 42 for board. The XY stage 32 for X-ray detection to which the X-ray detection device 1 is fixed is secured to the Z-axis driving mechanism 39 for X-ray detection. Further, the Z-axis driving mechanism 39 for X-ray detection is attached to the X-axis driving mechanism 43 for X-ray detection and the Y-axis driving mechanism 44 for X-ray detection. Accordingly, the X-ray inspection device of the third embodiment can transfer any spatial position within the transfer range by the X-axis driving mechanism 43 for X-ray detection, the Y-axis driving mechanism 44 for X-ray detection and the Z-axis driving mechanism 39 for X-ray detection. In FIG. 12, a circle Q indicated by a broken line represents a track of the center point of the board holding mechanism 40 and a circle R represents a track of the center point of a detection plane of the X-ray detection device 1.

Figure 14:
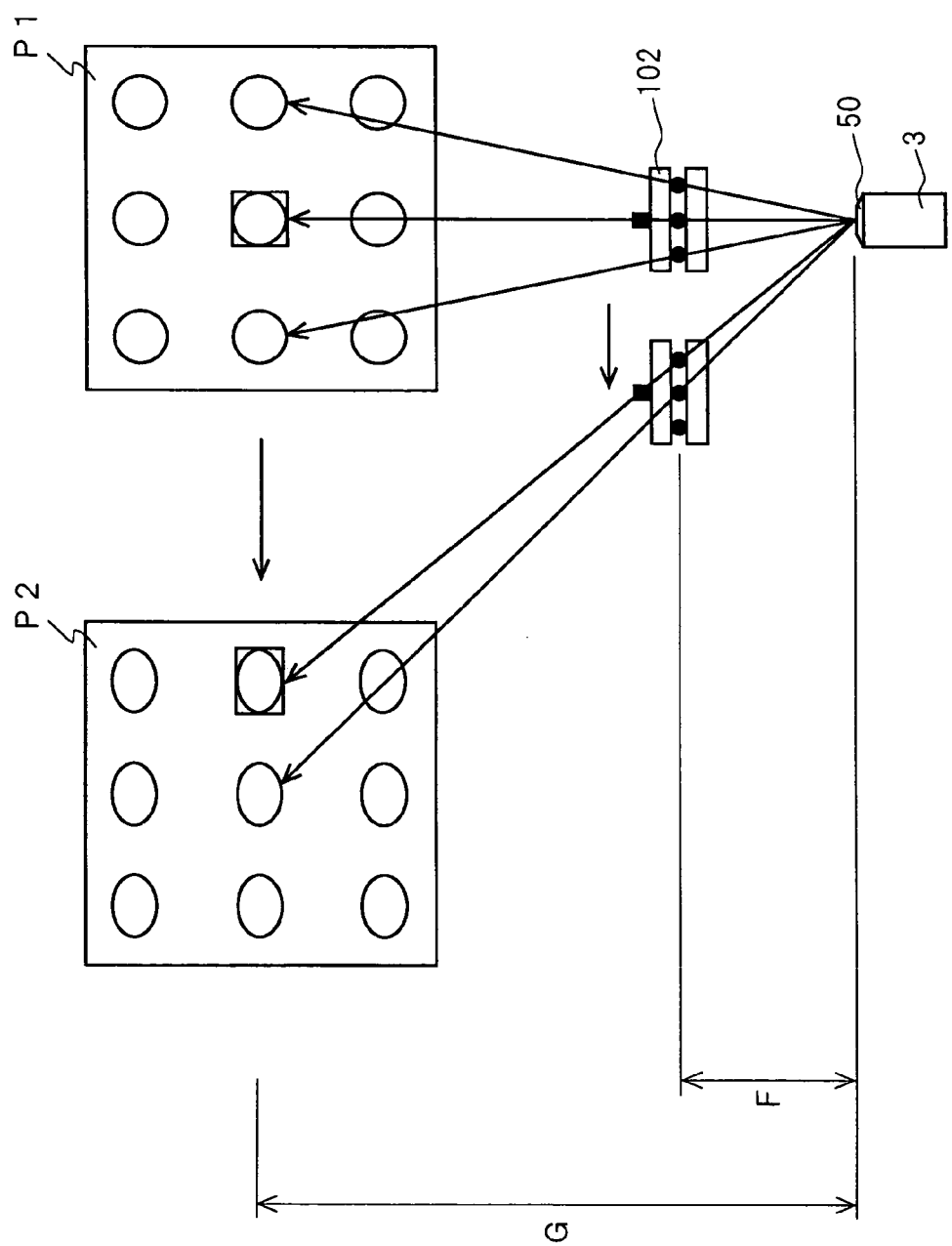
FIG. 14 is an explanation view of radiography in the X-ray inspection device in accordance with the third embodiment.

Next, radiography in the X-ray inspection device of the third embodiment will be described with reference to FIG. 14. FIG. 14 shows a printed circuit board having a ball grid array (hereinafter referred to as BGA) bonded part as the object to be inspected 102 and in FIG. 14, P1 and P2 represent X-ray images of the BGA bonded part.

In FIG. 14, the X-ray image P1 is an image obtained by fixing the printed circuit board (102) having the BGA bonded part to the XY stage 31 for board and seeing through in the vertical direction so that the ball bonded part at the center of the BGA bonded part is imaged at the center of the X-ray image of the X-ray detection device 1. At this time, a component with a low X-ray transmissivity such as a capacitor is mounted on the printed circuit board (102) having the BGA bonded part. This prevents the ball bonded part at the center of the BGA bonded part to be viewed. An X-ray image P2 is an image obtained by moving the printed circuit board (102) having the BGA bonded part to the left in FIG. 14 and further moving the X-ray detection device to the left so that the ball bonded part at the center of the BGA bonded part is located at the center of the X-ray image to be taken. In the X-ray image P2, since the component with a low X-ray transmissivity such as a capacitor does not overlap the central ball bonded part, the ball bonded part at the center of the BGA bonded part can be viewed.

To transfer the printed circuit board (102) and the X-ray detection device 1, the operator only pushes a switch of an operation device 60 (indicated by a block in FIG. 13) for transferring the object to be inspected 102 in the X-axis direction and/or the Y-axis direction, thereby automatically transferring the XY stage 32 for X-ray detection depending on the transfer amount of the object to be inspected 102. At this time, the XY stage 32 for X-ray detection transfers by the distance obtained by multiplying the transfer amount of the board holding mechanism 40 on the XY stage 31 for board by the magnifying factor of radiography. As a result, the ball bonded part at the center of the BGA bonded part is located at the center of the X-ray image at all times. Here, the magnifying factor of radiography is represented as G/F; where G is a distance between the X-ray focus 50 and the image forming position of the X-ray detection device 1, and F is a distance between the X-ray focus 50 and the detection position of the object to be inspected 102. In the case where the X-ray detection device 1 is transferred by the Z-axis driving mechanism 39 for X-ray detection and therefore the magnifying factor changes, the magnifying factor is recalculated and the XY stage 32 for X-ray detection is operated according to the recalculated magnifying factor.

As described above, the X-ray inspection device of the third embodiment is configured so that the XY stage 32 for X-ray detection is transferred automatically according to the transfer amount of the board holding mechanism 40 of the XY stage 31 for board and therefore the point to be viewed is located at the center of the X-ray image at all times.

Next, X-ray tomographic inspection methods in the X-ray inspection device of the third embodiment thus constituted will be described with reference to FIG. 15 to FIG. 17. There are two X-ray tomographic inspection methods in the X-ray inspection device of the third embodiment.

[First X-Ray Tomographic Inspection Method]

Firstly, a first X-ray tomographic inspection method will be described with reference to FIG. 15 and FIG. 16. FIG. 15 is an explanation view of X-ray tomography in the X-ray inspection device in accordance with the third embodiment. FIG. 16 shows an X-ray image P3 taken according to the first X-ray tomographic inspection method in the X-ray inspection device of the third embodiment.

Figure 15:
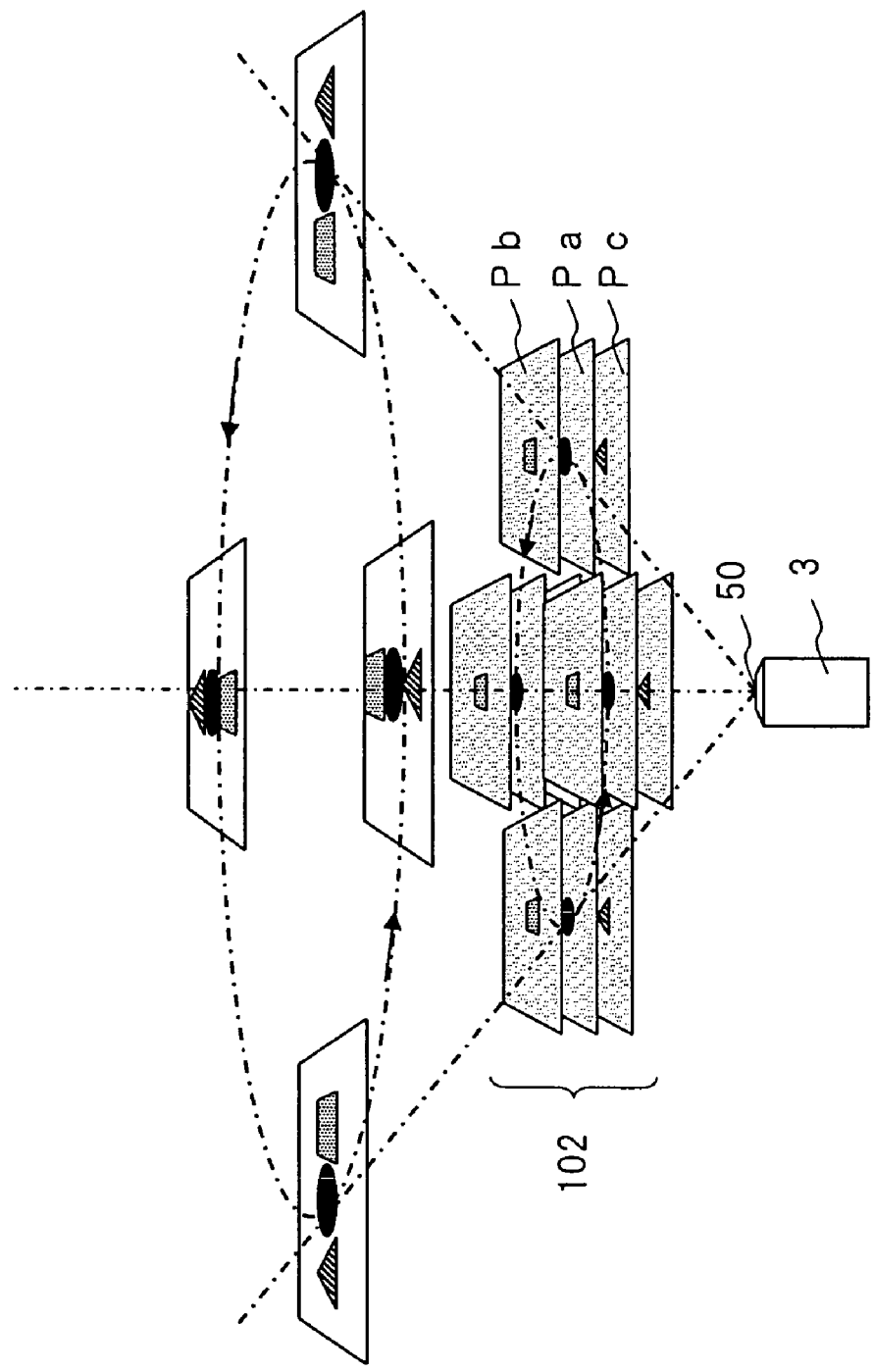
FIG. 15 is an explanation view of X-ray tomography in the X-ray inspection device in accordance with the third embodiment.
Figure 16:
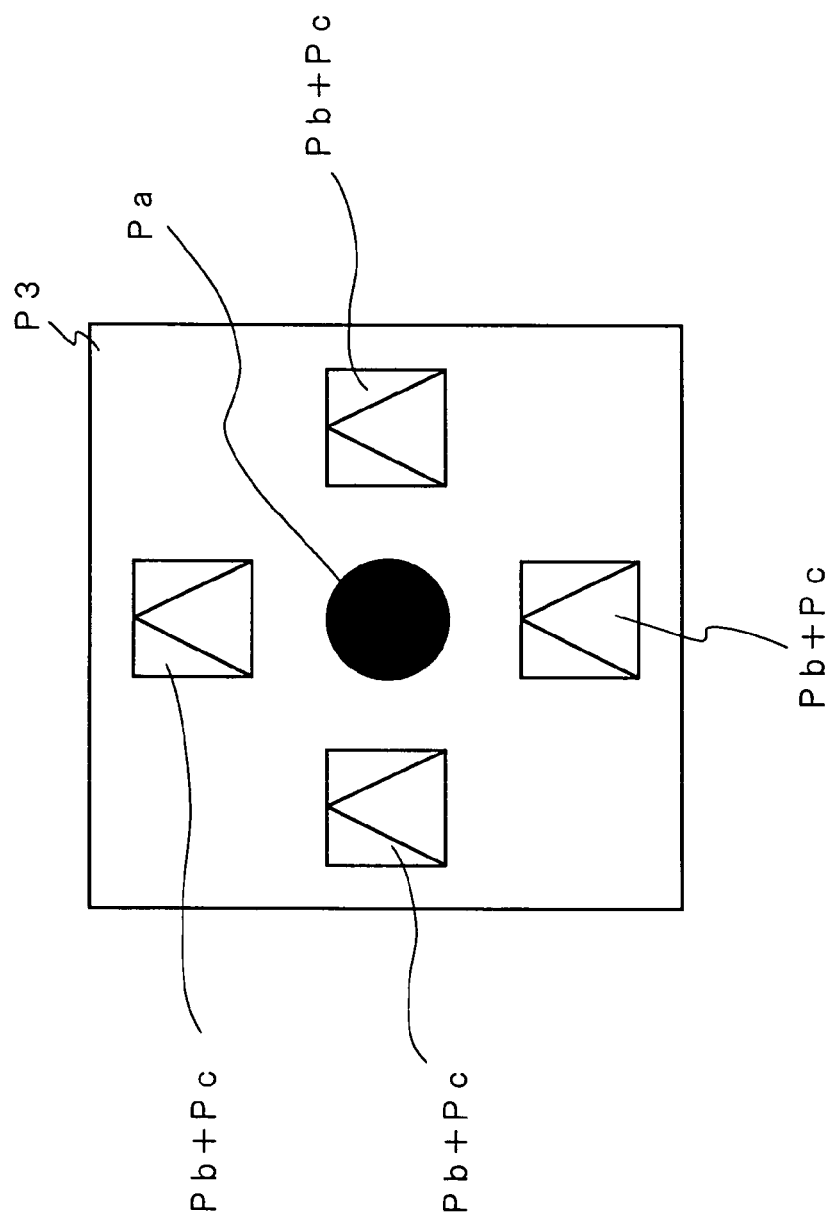
FIG. 16 is an explanation view of a first X-ray tomography in the X-ray inspection device in accordance with the third embodiment.

The object to be inspected 102 in FIG. 15 shows a three-layered printed circuit board as an example. As a three-layer structure, this printed circuit board consists of a circular pattern Pa on an intermediate layer as an observance plane, a square pattern Pb above the intermediate layer and a triangular pattern Pc below the intermediate layer. This printed circuit board is attached to the board holding mechanism 40 of the XY stage 31 for board and the board holding mechanism 40 of the XY stage 31 for board performs circular motion on the horizontal plane by the X-axis driving mechanism 41 for board and the Y-axis driving mechanism 42 for board. At this time, the XY stage 32 for X-ray detection is automatically transferred by the distance obtained by multiplying the transfer amount of the board holding mechanism 40 by the magnifying factor of radiography. As a result, the XY stage 32 for X-ray detection performs circular motion with a diameter obtained by multiplying the diameter of the circular motion by the board holding mechanism 40 by the magnifying factor of radiography. In calculating the above-mentioned magnifying factor, a distance between the X-ray focus 50 and a target position as the observation plane of the object to be inspected 102 is calculated as a distance between the X-ray focus 50 and the circular pattern Pa on the intermediate layer of the printed circuit plane. In this way, as shown in the X-ray image P3 in FIG. 16, the circular pattern Pa of the three-layered printed circuit board is imaged at the center of the X-ray image by the X-ray detection device 1 at all times. In this radiography operation, the center of the printed circuit board as the object to be inspected 102 and the center of rotation movement are located on the vertical line that passes the X-ray focus 50. In this rotation movement of the X-ray detection device 1, each axis motor for driving the corresponding XY stage 31 for board and the XY stage 32 for X-ray detection is synchronously controlled by the motor control device 37 so that the rotation angle of the XY stage 31 for board is the same as that of the XY stage 32 for X-ray detection at all times.

The X-ray detection device 1 of the third embodiment has the configuration in which a gray image in proportion to product of the time during which a shutter is opened and the X-ray intensity can be obtained by using a storage-type camera. The X-ray image P3 shown in FIG. 16 is an X-ray image taken with the shutter being opened while the printed circuit board and the X-ray detection device 1 performs circular motion by one rotation. If the shutter of the camera is opened at the rotation angle of 0 degree and closed upon one rotation, in the X-ray image of the printed circuit board, the circular pattern Pa is projected at the center of the X-ray image at all times and a clear pattern is radiographed. On the contrary, since the square pattern Pb and the triangular pattern Pc on the other cross sections are projected at different positions of the X-ray image according to rotation movement, a blur occurs in the image, resulting in an unclear image.

Therefore, by performing the first X-ray tomographic inspection method using the X-ray detection device 1 of the third embodiment, a synthesized horizontal tomographic image is formed and the condition of the designated cross section of the object to be inspected 102 can be inspected reliably.

[Second X-Ray Tomographic Inspection Method]

Next, a second X-ray tomographic inspection method in the X-ray inspection device in accordance with the third embodiment will be described with reference to FIG. 15 and FIG. 17.

In the above-mentioned first X-ray tomographic inspection method, one image is taken by opening the shutter during circular motion of one rotation of the printed circuit board as the object to be inspected 102 and the X-ray detection device 1. In the second X-ray tomographic inspection method, the printed circuit board and the X-ray detection device 1 are stopped at each certain angle in circular motion and radiography is performed once under the static state. Accordingly, in the second X-ray tomographic inspection method, radiography is performed plural times during circular motion of one rotation and a plurality of X-ray images are created. As a result, by overlapping the plurality of X-ray images, the second X-ray tomographic inspection method can obtain a synthesized horizontal tomographic image as in the above-mentioned first X-ray tomographic inspection method.

Also in the second X-ray tomographic inspection method, the three-layered printed circuit board shown in FIG. 15 is described as the object to be inspected 102.

The printed circuit board is attached to the board holding mechanism 40 of the XY stage 31 for board. At the beginning of radiography operation, the XY stage 31 for board transfers to the predetermined position at the angle of 0 degree on the circumference in circular motion on the horizontal plane of the object to be inspected 102 and stops there. At this time, the XY stage 32 for X-ray detection transfers automatically by the distance obtained by multiplying the transfer amount of the XY stage 31 for board by the magnifying factor of radiography. Radiography is performed under this state to create a first X-ray image. Next, the XY stage 31 for board is transferred to the predetermined position at a desired angle on the circumference in circular motion and stopped there and then radiography is performed. Subsequently, radiography is performed each time when the XY stage 31 for board transfers by the desired angle on the circumference in circular motion. By taking X-ray images in this manner, at all stop positions on the circumference in circular motion, the circular pattern Pa of the three-layered printed circuit board is imaged at the center of the X-ray image by the X-ray detection device 1 at all times.

As described above, in the second X-ray tomographic inspection method, the center point of circular motion of the printed circuit board as the object to be inspected 102 and the center point of circular motion of the X-ray detection device 1 are located on the vertical line that passes the X-ray focus 50. At the positions on the circumference in each circular motion of the printed circuit board and the X-ray detection device 1, the central angle in each circle are the same at all times. In this manner, the X-axis motor 33 for board 33, the Y-axis motor 34 for board, the X-axis motor 35 for X-ray detection and the Y-axis motor 36 for X-ray detection are controlled by the motor control device 37 so that the printed circuit board and the X-ray detection device 1 perform circular motion in synchronization with each other.

Similarly to the first X-ray tomographic inspection method, in the second X-ray tomographic inspection method, a gray image of the X-ray image in proportion to the product of the time during which a shutter is opened and the X-ray intensity is created by the X-ray detection device 1. However, in the second X-ray tomographic inspection method, it is more preferable to use a high sensitive camera since the shutter is opened for a short time.

Figure 17:
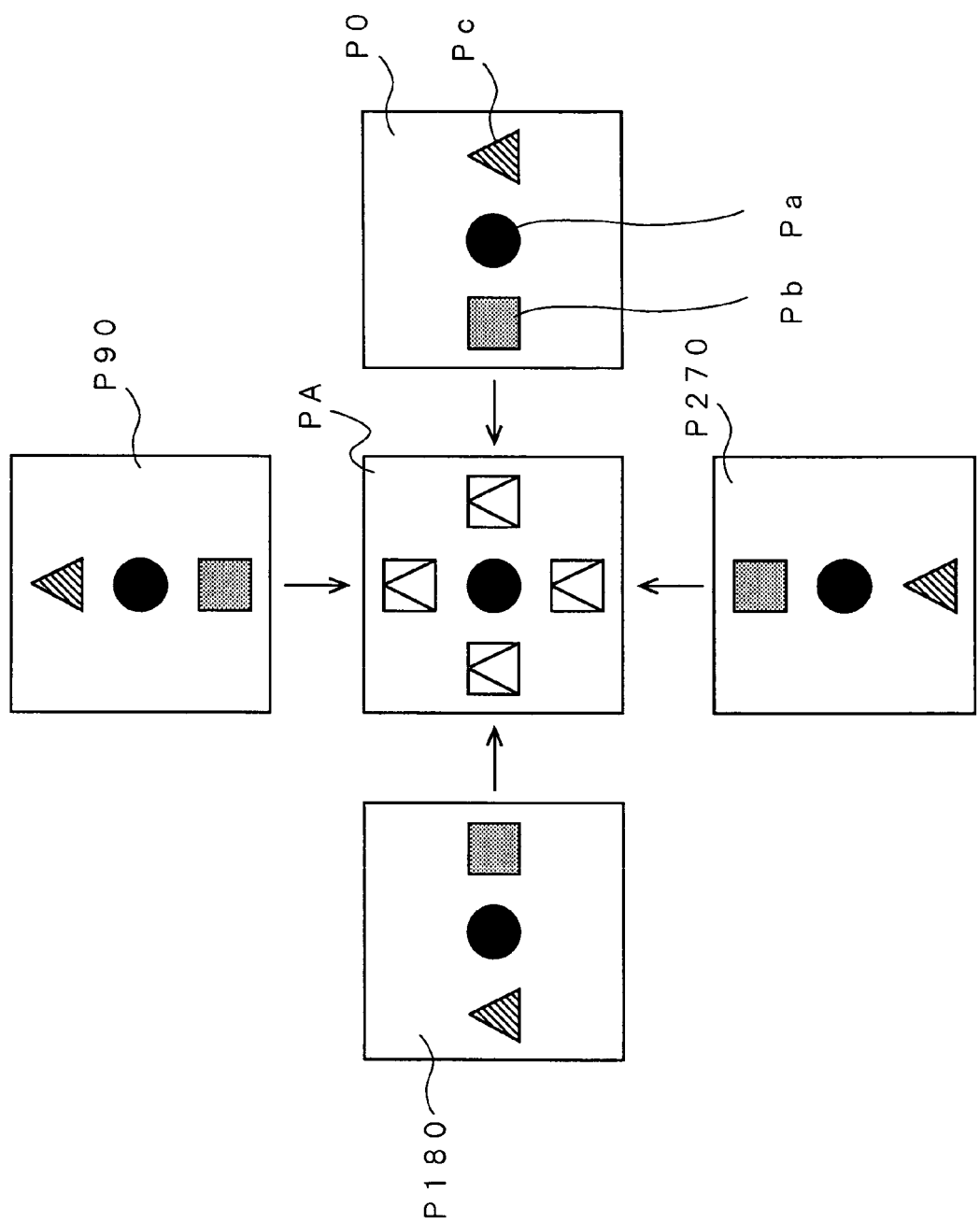
FIG. 17 is an explanation view of a second X-ray tomography in the X-ray inspection device in accordance with the third embodiment.

FIG. 17 is an example in which the printed circuit board and the X-ray detection device 1 are stopped each 90 degrees and imaged to create four X-ray images. In FIG. 17, a P0 is an X-ray image at an angle of 0 degree, a P90 is an X-ray image at an angle of 90 degrees, a P180 is an X-ray image at an angle of 180 degrees and a P270 is an X-ray image at an angle of 270 degrees. A PA illustrated at the center of FIG. 17 is a synthesized X-ray image as well as a synthesized horizontal tomographic image formed by overlapping the four X-ray images in an image processing device 70 (indicated by a block in FIG. 13) in the X-ray inspection device of the third embodiment.

In the second X-ray tomographic inspection method, by increasing the number of stopped positions during circular motion, taking the X-ray image at reduced stopped angles to create a lot of X-ray images, and synthesizing these images, further clearer X-ray image can be acquired. However, since the time for radiograph is increased with increase in stopped positions, performing the X-ray inspection requires longer time.

In the second X-ray tomographic inspection method, by calculating for reconstruction of the X-ray image according to CT technology using information on a plurality of X-ray images obtained each desired angle in the image processing device 70, a three-dimensional stereoscopic image can be also created. By using thus created stereoscopic image, it becomes possible to accurately detect information on each cross section of the object to be inspected 102. Therefore, according to the second X-ray tomographic inspection method, internal information on each cross section of the object to be inspected 102 can be easily inspected without axis movement.

As described above, according to the X-ray inspection device of the third embodiment, the inspected place of the object to be inspected 102 can be viewed from any direction within the range of X-ray irradiation angles, and even if the magnifying factor is changed, the same inspected place can be viewed at all times and only the image on horizontal cross section including the inspected place can be extracted. Moreover, according to the X-ray inspection device of the third embodiment, information on each cross section layer of the object to be inspected 102 can be easily obtained.

According to the X-ray inspection device of the third embodiment, by the X-ray irradiation device 3 and the X-ray detection device 1 that fixes the X-ray focus, the inspected place as a target of X-ray inspection can be viewed without shifting from the center of the monitor screen while changing radiographic direction and radiographic magnifying factor. Further, according to the X-ray inspection device of the third embodiment, by synthesizing horizontal tomographic images of the inspected place, various bonding defects including open defect of the bonded part of the printed circuit board can be inspected.

As described in each embodiment in detail, the X-ray inspection device of the present invention can easily obtain clear information of the cross section of the object to be inspected with high resolution at lower cost and accurate inspection based on the cross-sectional information can be performed.

In these years, in the market of electronic equipment such as personal digital instrument, there has been a strong demand for decrease in size and weight of products, and circuit boards constituting electronic equipment have also been strongly required to decrease in size and weight. For this reason, linear-bond type electronic components such as QFP (Quad Flat Package) and SOP (Small Outline Package), which arrange an electrode lead on the periphery of the conventional package, and area-bond type electronic components such as BGA (Ball Grid Array) and CSP (Chip Size Package), which arrange a pole electrode and the like on the whole back face of the package, have been widely used. Since the area-bond type package can have more electrodes within a narrow area than the linear-bond type can, the circuit board can be miniaturized advantageously. However, it cannot an optical visual inspection device as the bonded part cannot be viewed from outside. Thus, for the bonding inspection of these components, radiography capable of seeing through the inner condition of the circuit board has been increasingly used. The X-ray inspection device of the present invention is useful for these components.

Although the invention has been described in its preferred form with a certain degree of particularity, it is understood that the present disclosure of the preferred form has been changed in the details of construction and the combination and arrangement of parts may be resorted to without departing from the spirit and the scope of the invention as claimed.

The invention claimed is:

1. An X-ray inspection device comprising:
an X-ray irradiation device for generating an X-ray and irradiating an object to be inspected with the X-ray;
an X-ray detection device for detecting the X-ray radiated from said X-ray irradiation device that passes through said object to be inspected;
a swinging device having a holding plane for holding said object to be inspected in an X-ray path from said X-ray irradiation device to said X-ray detection device and driving said holding plane at an optional angle in an optional direction with respect to an X-ray irradiation axis which is arranged on said X-ray path; and
a control device for controlling driving of said swinging device and said X-ray irradiation device, receiving an input of an X-ray image data from said X-ray detection device and displaying said X-ray image data,
wherein said holding plane is composed to swing said holding plane by rotating around two axes orthogonal to each other by an X-axis motor and a Y-axis motor, rotation by said X-axis motor is reciprocating motion reciprocating within a predetermined range of rotation angles and rotation by said Y-axis motor performs reciprocating motion of the same cycle within a predetermined range of rotation angles with the phase being shifted from the rotation of said X-axis motor.

2. The X-ray inspection device in accordance with claim 1, wherein said control device controls driving of said X-ray detection device, said swinging device and said X-ray irradiation device and displays data on the X-ray image from said X-ray detection device and data on an arbitrary cross section from said X-ray image data.

3. The X-ray inspection device in accordance with claim 1, wherein said control device calculates inner condition of said object to be inspected in comparison with prestored data and has an automatic inspection function or inspecting inner condition of said object to be inspected.

4. An X-ray inspection device comprising:
an X-ray irradiation device for generating an X-ray and irradiating an object to be inspected with the X-ray;
an X-ray detection device for detecting the X-ray radiated from said X-ray irradiation device that passes through said object to be inspected;
a swinging device having a holding plane for holding said object to be inspected in an X-ray path from said X-ray irradiation device to said X-ray detection device and driving said object to be inspected at an arbitrary angle in an arbitrary direction with respect to an X-ray irradiation axis which is arranged on said X-ray path;
a swinging device for X-ray detection for driving said X-ray detection device in the same direction and at the same angle as said object to be inspected driven by said swinging device; and
a control device for controlling driving of said swinging device and said X-ray irradiation device, receiving an input of an X-ray image data from said X-ray detection device and displaying said X-ray image data,
wherein said holding plane is composed to swing said holding plane by rotating around two axes orthogonal to each other by an X-axis motor and a Y-axis motor, rotation by said X-axis motor is reciprocating motion reciprocating within a predetermined range of rotation angles and rotation by said Y-axis motor performs reciprocating motion of the same cycle within a predetermined range of rotation angles with the phase being shifted from the rotation of said X-axis motor.

5. The X-ray inspection device in accordance with claim 4, wherein said control device controls driving of said X-ray detection device, said swinging device, said swinging device for X-ray detection and said X-ray irradiation device, stops and images said object to be inspected at an arbitrary position and displays data on the X-ray image from said X-ray detection device and data on an arbitrary cross section from said X-ray image data.

6. The X-ray inspection device in accordance with claim 4, wherein said control device calculates inner condition of said object to be inspected in comparison with prestored data and has an automatic inspection function of inspecting inner condition of said object to be inspected.

7. An X-ray inspection device comprising:
an X-ray irradiation device for irradiating an X-ray in the vertical direction in a form of cone with an X-ray focus as a vertex at a predetermined irradiation angle;
a holding mechanism for horizontally holding an object to be inspected within an X-ray irradiation range
a transfer mechanism for object to be inspected for transferring said object to be inspected held by said holding mechanism to an arbitrary position in the horizontal direction within the X-ray irradiation range;
an X-ray detection device having a detection plane for detecting the X-ray that passes through said object to be inspected;
a transfer mechanism for X-ray detection for transferring said X-ray detection device to an arbitrary position on a plain parallel to the plane to which said object to be inspected is transferred;
a motor control device for controlling driving of said transfer mechanism for object to be inspected and said transfer mechanism for X-ray detection in synchronization with each other;
an image processing device for extracting an X-ray image of an arbitrary cross section from the X-ray image formed by said X-ray detection device; and
a display device for displaying said X-ray image formed by said X-ray detection device and said image processing device,
wherein when said transfer mechanism for object to be inspected transfers said object to be inspected within the X-ray irradiation range, said transfer mechanism for object to be inspected and said transfer mechanism for X-ray detection are transferred in synchronization with each other so that a center point of said detection plane of said X-ray detection device is located on a straight line connecting said X-ray focus with a center point of an inspected place of said object to be inspected.

8. The X-ray inspection device in accordance with claim 7, wherein said transfer mechanism for X-ray detection has a Z-axis driving mechanism for X-ray detection for transferring said X-ray detection device in the vertical direction and a magnifying factor of the X-ray image can be changed by changing a ratio between a distance from said X-ray focus to said object to be inspected and a distance from said X-ray focus to said X-ray detection device.

9. The X-ray inspection device in accordance with claim 8, wherein when said Z-axis driving mechanism for X-ray detection transfers said transfer mechanism for X-ray detection in the vertical direction, said transfer mechanism for X-ray detection is transferred in synchronization with said Z-axis driving mechanism for X-ray detection so that a center point of said X-ray detection device is located on a straight line connecting said X-ray focus with a center point of an inspected place of said object to be inspected.

10. An X-ray inspection device comprising:
an X-ray irradiation device for irradiating an X-ray in the vertical direction in a form of cone with an X-ray focus as a vertex at a predetermined irradiation angle;
a holding mechanism for horizontally holding an object to be inspected within an X-ray irradiation range;
a transfer mechanism for object to be inspected for transferring said object to be inspected held by said holding mechanism to an arbitrary position in the horizontal direction within an X-ray irradiation range;
an X-ray detection device having a detection plane for detecting the X-ray that passes through said object to be inspected;
a transfer mechanism for X-ray detection for transferring said X-ray detection device to an arbitrary position on a plain parallel to the plane to which said object to be inspected is transferred;
a motor control device for controlling driving of said transfer mechanism for object to be inspected and said transfer mechanism for X-ray detection in synchronization with each other;
an image processing device for extracting an X-ray image of an arbitrary cross section from the X-ray image formed by said X-ray detection device; and
a display device for displaying said X-ray image formed by said X-ray detection device and said image processing device,
wherein said transfer mechanism for object to be inspected and said transfer mechanism for X-ray detection are rotated on each horizontal plane in synchronization with each other and radiography is performed while a shutter is opened during one rotation in rotation motion.

11. An X-ray inspection device comprising:
an X-ray irradiation device for irradiating an X-ray in the vertical direction in a form of cone with an X-ray focus as a vertex at a predetermined irradiation angle;
a holding mechanism for horizontally holding an object to be inspected within an X-ray irradiation range;
a transfer mechanism for object to be inspected for transferring said object to be inspected held by said holding mechanism to an arbitrary position in the horizontal direction within an X-ray irradiation range;
an X-ray detection device having a detection plane for detecting the X-ray that passes through said object to be inspected;
a transfer mechanism for X-ray detection for transferring said X-ray detection device to an arbitrary position on a plain parallel to the plane to which said object to be inspected is transferred;
a motor control device for controlling driving of said transfer mechanism for object to be inspected and said transfer mechanism for X-ray detection in synchronization with each other;
an image processing device for extracting an X-ray image of an arbitrary cross section from the X-ray image formed by said X-ray detection device; and
a display device for displaying said X-ray image formed by said X-ray detection device and said image processing device,
wherein said transfer mechanism for object to be inspected and said transfer mechanism for X-ray detection are rotated on each horizontal plane in synchronization with each other while stopping by each certain angle and radiography is performed at each stopped position.

12. An X-ray inspection method using an X-ray inspection device which comprises at least a swinging device having a holding plane for holding said object to be inspected in an X-ray path from said X-ray irradiation device to said X-ray detection device and driving said holding plane at an optional angle in an optional direction with respect to an X-ray irradiation axis which is arranged on said X-ray path, and said X-ray inspection method comprising:
attaching an object to be inspected to a swinging device disposed on an X-ray path from an X-ray irradiation device to an X-ray detection device;
driving said object to be inspected by said swinging device at an arbitrary angle in an arbitrary direction with respect to an X-ray irradiation axis on said X-ray path;
irradiating said object to be inspected with the X-ray radiated from said X-ray irradiation device;
detecting the X-ray that passes through said object to be inspected by said X-ray detection device; and
receiving an input of an X-ray image data from said X-ray detection device and extracting data on an arbitrary cross section from said X-ray image data;
wherein said holding plane to which said object to be inspected is attached is swung by two axes orthogonal to each other by an X-axis motor and a Y-axis motor, rotation by said X-axis motor is reciprocating motion reciprocating within a predetermined range of rotation angles and rotation by said Y-axis motor performs reciprocating motion of the same cycle within a predetermined range of rotation angles with the phase being shifted from the rotation of said X-axis motor.

13. An X-ray inspection method comprising:
holding an object to be inspected horizontally within an X-ray irradiation range;
transferring said object to be inspected held by said holding mechanism to an arbitrary position in the horizontal direction within an X-ray irradiation range;
transferring said X-ray detection device to an arbitrary position on a plain parallel to the plane to which said object to be inspected is transferred by a transfer mechanism for X-ray detection so that a target point is located at a center of the X-ray image formed by an X-ray detection device in synchronization with the transfer of said object to be inspected;
irradiating an X-ray in the vertical direction in a form of cone with an X-ray focus as a vertex at a predetermined irradiation angle;
detecting the X-ray that passes through said object to be inspected by said X-ray detection device;
in an image processing device, extracting an X-ray image of an arbitrary cross section from the X-ray image formed by said X-ray detection device; and
displaying said X-ray image formed by said X-ray detection device and said image processing device,
wherein when said transfer mechanism for object to be inspected transfers said object to be inspected within the X-ray irradiation range, said transfer mechanism for object to be inspected and said transfer mechanism for X-ray detection are transferred in synchronization with each other so that a center point of said detection plane of said X-ray detection device is located on a straight line connecting said X-ray focus with a center point of an inspected place of said object to be inspected.

* * * * *